(12) United States Patent
Mandelboim et al.

(10) Patent No.: US 12,121,579 B2
(45) Date of Patent: Oct. 22, 2024

(54) ANTIBODIES SPECIFIC TO HUMAN T-CELL IMMUNOGLOBULIN AND ITIM DOMAIN (TIGIT)

(71) Applicants: YISSUM RESEARCH DEVELOPMENT COMPANY OF THE HEBREW UNIVERSITY OF JERUSALEM LTD., Jerusalem (IL); UNIVERSITY OF RIJEKA FACULTY OF MEDICINE, Rijeka (HR)

(72) Inventors: Ofer Mandelboim, Shoham (IL); Noa S. Kaynan, Kibbutz Barkai (IL); Pinchas Tsukerman, Jerusalem (IL); Stipan Jonjic, Rijeka (HR)

(73) Assignees: YISSUM RESEARCH DEVELOPMENT COMPANY OF THE HEBREW UNIVERSITY OF JERUSALEM LTD., Jerusalem (IL); UNIVERSITY OF RIJEKA FACULTY OF MEDICINE, Rijeka (HR)

( * ) Notice: Subject to any disclaimer, the term of this patent is extended or adjusted under 35 U.S.C. 154(b) by 799 days.

(21) Appl. No.: 17/168,451

(22) Filed: Feb. 5, 2021

(65) Prior Publication Data

US 2021/0220472 A1 Jul. 22, 2021

Related U.S. Application Data

(62) Division of application No. 15/756,606, filed as application No. PCT/IL2016/050952 on Sep. 1, 2016, now Pat. No. 10,946,095.

(60) Provisional application No. 62/314,427, filed on Mar. 29, 2016, provisional application No. 62/213,140, filed on Sep. 2, 2015.

(51) Int. Cl.
| | |
|---|---|
| *C07K 16/28* | (2006.01) |
| *A61K 39/395* | (2006.01) |
| *A61P 35/00* | (2006.01) |
| *C12N 5/10* | (2006.01) |
| *C12N 15/00* | (2006.01) |
| *C12N 15/63* | (2006.01) |
| *G01N 33/577* | (2006.01) |
| *A61K 39/00* | (2006.01) |

(52) U.S. Cl.
CPC ........ *A61K 39/39558* (2013.01); *A61P 35/00* (2018.01); *C07K 16/28* (2013.01); *C07K 16/2803* (2013.01); *G01N 33/577* (2013.01); *A61K 2039/505* (2013.01); *C07K 2317/24* (2013.01); *C07K 2317/76* (2013.01); *C07K 2317/92* (2013.01); *C12N 5/10* (2013.01); *C12N 15/00* (2013.01); *C12N 15/63* (2013.01)

(58) Field of Classification Search
CPC .. A61K 39/395; C07K 16/28; C07K 16/2803; C07K 2317/24; C07K 2317/76; C07K 2317/92
See application file for complete search history.

(56) References Cited

U.S. PATENT DOCUMENTS

| | | | |
|---|---|---|---|
| 4,816,567 A | 3/1989 | Cabilly | |
| 4,946,778 A | 8/1990 | Ladner | |
| 5,225,539 A | 7/1993 | Winter | |
| 5,585,089 A | 12/1996 | Queen | |
| 5,641,870 A | 6/1997 | Rinderknecht | |
| 5,869,337 A | 2/1999 | Crabtree | |
| 5,910,573 A | 6/1999 | Andreas | |
| 7,193,069 B2 | 3/2007 | Takao | |
| 7,579,392 B2 | 8/2009 | Gan | |
| 8,110,369 B2 | 2/2012 | Rump | |
| 8,591,893 B2 | 11/2013 | Wadhwa | |
| 2009/0324491 A1 | 12/2009 | Aburatani | |
| 2013/0251720 A1 | 9/2013 | Clark | |
| 2015/0152160 A1 | 6/2015 | Gao | |

FOREIGN PATENT DOCUMENTS

| | | |
|---|---|---|
| CN | 103073644 A | 5/2013 |
| EP | 0404097 A2 | 12/1990 |
| EP | 1516629 A2 | 3/2005 |
| EP | 2070548 A1 | 6/2009 |
| EP | 2170953 B1 | 7/2015 |
| GB | 2408508 A | 6/2005 |
| WO | 9311161 A1 | 6/1993 |
| WO | 9315210 A1 | 8/1993 |
| WO | 9613583 A2 | 5/1996 |
| WO | 9637621 A2 | 11/1996 |
| WO | 9963063 A1 | 12/1999 |

(Continued)

OTHER PUBLICATIONS

Murphy et al., Journal of Immunological Methods, vol. 463, p. 127-133, 2018.*

(Continued)

*Primary Examiner* — Hong Sang

(74) *Attorney, Agent, or Firm* — RAPHAEL BELLUM PLLC

(57) ABSTRACT

Natural killer (NK) cell killing of various tumors is inhibited in the presence of ligands of TIGIT, an inhibitory receptor present on all human NK cells and on various T cells. Monoclonal antibodies that recognize TIGIT and inhibit its suppressive activity on T-cells are provided as well as pharmaceutical compositions comprising them and methods for their use in cancer immunotherapy and in diagnosis and treatment of immune disorders.

16 Claims, 14 Drawing Sheets

Specification includes a Sequence Listing.

(56) References Cited

FOREIGN PATENT DOCUMENTS

| | | | |
|---|---|---|---|
| WO | 2004024068 A2 | 3/2004 | |
| WO | 2004024072 A2 | 3/2004 | |
| WO | 2004050870 A2 | 6/2004 | |
| WO | 2004074324 A2 | 9/2004 | |
| WO | 2005052005 A1 | 6/2005 | |
| WO | 2006042240 A2 | 4/2006 | |
| WO | 2006124667 A2 | 11/2006 | |
| WO | 2007110694 A2 | 10/2007 | |
| WO | 2008146854 A1 | 12/2008 | |
| WO | 2009088105 A1 | 7/2009 | |
| WO | 2009126688 A2 | 10/2009 | |
| WO | 2014106629 A1 | 7/2014 | |
| WO | 2014106631 A1 | 7/2014 | |
| WO | 2015009856 A2 | 1/2015 | |
| WO | 2016028656 A1 | 2/2016 | |
| WO | 2016036319 A1 | 3/2016 | |
| WO | 2016145317 A1 | 9/2016 | |
| WO | 2016191643 A2 | 12/2016 | |
| WO | 2017118972 A1 | 7/2017 | |

OTHER PUBLICATIONS

McCafferty et al., (1990) Phage antibodies: filamentous phage displaying antibody variable domains. nature, 348 (6301), 552-554.
Morimoto & Inouye, (1992) Single-step purification of F (ab') 2 fragments of mouse monoclonal antibodies (immunoglobulins G1) by hydrophobic interaction high performance liquid chromatography using TSKgel Phenyl-5PW. Journal of biochemical and biophysical methods, 24(1-2), 107-117.
Mueller et al., (1998) A dimeric bispecific miniantibody combines two specificities with avidity. FEBS letters, 432(1-2), 45-49.
Ota et al., (2004) Complete sequencing and characterization of 21,243 full-length human cDNAs. Nature genetics, 36(1), 40-45.
Paine-Murrieta et al., (1997) Human tumor models in the severe combined immune deficient (scid) mouse. Cancer chemotherapy and pharmacology, 40(3), 209-214.
Presta et al., (1993) Humanization of an antibody directed against IgE. The Journal of Immunology, 151(5), 2623-2632.
Riechmann et al., (1988) Reshaping human antibodies for therapy. Nature, 332(6162), 323-327.
Rubinstein et al., (2013) Fusobacterium nucleatum promotes colorectal carcinogenesis by modulating E-cadherin/β-catenin signaling via its FadA adhesin. Cell host & microbe, 14(2), 195-206.
Rudikoff et al., (1982) Single amino acid substitution altering antigen-binding specificity. Proc Natl Acad Sci U S A 79 (6): 1979-1983.
Sears & Garrett, (2014) Microbes, microbiota, and colon cancer. Cell host & microbe, 15(3), 317-328.
Seidel et al., (2012) Virus-mediated inhibition of natural cytotoxicity receptor recognition. Cellular and molecular life sciences, 69(23), 3911-3920.
Seth et al., (2005) "The Poliovirus receptor/CD155 is a potential modulator of the T cell response". Immunobiology 210(6-8): 542. Joint Annual Meeting of the German and Scandinavian Societies of Immunology; Kiel, Germany; Sep. 21-24, 2005, ISSN 0171-2985, XP009074924.
Sims et al., (1993) A humanized CD18 antibody can block function without cell destruction. The Journal of Immunology, 151(4), 2296-2308.
Smyth et al., (2001) A fresh look at tumor immunosurveillance and immunotherapy. Nature immunology, 2(4), 293-299.
Sobhani et al., (2011) Microbial dysbiosis in colorectal cancer (CRC) patients. PloS one, 6(1), e16393, 1-7.
Stanietsky et al., (2009) The interaction of TIGIT with PVR and PVRL2 inhibits human NK cell cytotoxicity. Proceedings of the National Academy of Sciences, 106(42), 17858-17863.
Stanietsky et al., (2013) Mouse TIGIT inhibits NK-cell cytotoxicity upon interaction with PVR. European journal of Immunology, 43(8), 2138-2150.

Strauss et al., (2011) Invasive potential of gut mucosa-derived Fusobacterium nucleatum positively correlates with IBD status of the host. Inflammatory bowel diseases, 17(9), 1971-1978.
Tannock, (2008) The search for disease-associated compositional shifts in bowel bacterial communities of humans. Trends in microbiology, 16(10), 488-495.
Témoin et al., (2012) Identification of oral bacterial DNA in synovial fluid of arthritis patients with native and failed prosthetic joints. Journal of clinical rheumatology: practical reports on rheumatic & musculoskeletal diseases, 18(3), 117-121.
Vaughan et al., (1996) Human antibodies with sub-nanomolar affinities isolated from a large non-immunized phage display library. Nature biotechnology, 14(3), 309-314.
Verbovetski et al., (2002) Opsonization of apoptotic cells by autologous iC3b facilitates clearance by immature dendritic cells, down-regulates DR and CD86, and up-regulates CC chemokine receptor 7. Journal of Experimental Medicine, 196(12), 1553-1561.
Verhoeyen et al., (1988) Reshaping human antibodies: grafting an antilysozyme activity. Science, 239(4847), 1534-1536.
Vivier et al., (2011) Innate or adaptive immunity? The example of natural killer cells. Science, 331(6013), 44-49.
Ward et al., (1989) Binding activities of a repertoire of single immunoglobulin variable domains secreted from *Escherichia coli*. Nature, 341(6242), 544-546.
Wu & Kabat, (1970) An analysis of the sequences of the variable regions of Bence Jones proteins and myeloma light chains and their implications for antibody complementarity. The Journal of experimental medicine, 132(2), 211-250.
Xu et al., (2007) FadA from Fusobacterium nucleatum utilizes both secreted and nonsecreted forms for functional oligomerization for attachment and invasion of host cells. Journal of Biological Chemistry, 282(34), 25000-25009.
Yang et al., (2015) Uveal melanoma metastasis models. Ocular oncology and pathology, 1(3), 151-160.
Yu et al., (2009) The surface protein TIGIT suppresses T cell activation by promoting the generation of mature immunoregulatory dendritic cells. Nature immunology, 10(1), 48-57.
Zapata et al., (1995) Engineering linear F (ab') 2 fragments for efficient production in *Escherichia coli* and enhanced antiproliferative activity. Protein Engineering, Design and Selection, 8(10), 1057-1062.
Zimmermann et al., (2002) Relaxation, equilibrium oligomerization, and molecular symmetry of the VASP (336- 380) EVH2 tetramer. Biochemistry, 41(37), 11143-11151.
Structure and Function on Immunoglobulins. In: Fundamental Immunology, 3rd edition. Edited by Paul WE. Raven Press, LTD., New York, USA. 1993, pp. 292-295.
Bendig (1995) Humanization of rodent monoclonal antibodies by CDR grafting. Methods: A Companion to Methods in Enzymology 8: 83-93.
Besser et al., (2013) Adoptive Transfer of Tumor-Infiltrating Lymphocytes in Patients with Metastatic Melanoma: Intent-to-Treat Analysis and Efficacy after Failure to Prior Immunotherapies. Clin Cancer Res, 19(17), 4792-4800.
Bird et al., (1988) Single-chain antigen-binding proteins. Science, 242(4877), 423-426.
Borden, (2012) Transfected mesenchymal stem cells in a thermoreversible hydrogel matrix for the treatment of myocardial infarction (vol. 74, No. 03).
Brennan et al., (1985) Preparation of bispecific antibodies by chemical recombination of monoclonal immunoglobulin G1 fragments. Science, 229(4708), 81-83.
Brüggemann et al., (1993) Designer mice: the production of human antibody repertoires in transgenic animals. The Year in immunology, 7, 33-40.
Carter et al., (1992) High level *Escherichia coli* expression and production of a bivalent humanized antibody fragment. Nature Biotechnology, 10(2), 163-167.
Carter et al., (1992) Humanization of an anti-p185HER2 antibody for human cancer therapy. Proceedings of the National Academy of Sciences, 89(10), 4285-4289.

(56) References Cited

OTHER PUBLICATIONS

Castellarin et al., (2012) Fusobacterium nucleatum infection is prevalent in human colorectal carcinoma. Genome research, 22(2), 299-306.
Chaushu et al., (2012) Direct recognition of Fusobacterium nucleatum by the NK cell natural cytotoxicity receptor NKp46 aggravates periodontal disease. PLoS pathogens, 8(3), e1002601, 1-12.
Chauvin et al., (2015) TIGIT and PD-1 impair tumor antigen-specific CD8+ T cells in melanoma patients. The Journal of clinical investigation, 125(5), 2046-2058.
Chothia & Lesk, (1987) Canonical structures for the hypervariable regions of immunoglobulins. Journal of molecular biology, 196(4), 901-917.
Clackson et al., (1991) Making antibody fragments using phage display libraries. Nature, 352(6336), 624-628.
Coley, (1910) The treatment of inoperable sarcoma by bacterial toxins (the mixed toxins of the *Streptococcus erysipelas* and the Bacillus prodigiosus). Proceedings of the Royal Society of Medicine, 3(Surg_Sect), 1-48.
Colman (1994) Effects of amino acid sequence changes on antibody-antigen interactions. Res Immunol 145(1): 33-36.
Coppenhagen-Glazer et al., (2015) Fap2 of Fusobacterium nucleatum is a galactose-inhibitable adhesin involved in coaggregation, cell adhesion, and preterm birth. Infection and immunity, 83(3), 1104-1113.
Duchosal et al., (1992) Immunization of hu-PBL-SCID mice and the rescue of human monoclonal Fab fragments through combinatorial libraries. Nature, 355(6357), 258-262.
Elias et al., (2014) Immune evasion by oncogenic proteins of acute myeloid leukemia. Blood, 123(10), 1535-1543.
Fields et al., (2013) Creation of recombinant antigen-binding molecules derived from hybridomas secreting specific antibodies. Nature protocols, 8(6), 1125-1148.
Gardiner, (2008) Killer cell immunoglobulin-like receptors on NK cells: the how, where and why. International journal of Immunogenetics, 35(1), 1-8.
Gonen-Gross et al., (2010) Inhibitory NK receptor recognition of HLA-G: regulation by contact residues and by cell specific expression at the fetal-maternal interface. PLoS One, 5(1), e8941, 1-10.
Grange et al., (2008) The use of mycobacterial adjuvant-based agents for immunotherapy of cancer. Vaccine, 26(39), 4984-4990.
Gur et al., (2015) Binding of the Fap2 protein of Fusobacterium nucleatum to human inhibitory receptor TIGIT protects tumors from immune cell attack. Immunity, 42(2), 344-355.
Han & Wang, (2013) Mobile microbiome: oral bacteria in extra-oral infections and inflammation. Journal of dental research, 92(6), 485-491.
Han et al., (2004) Fusobacterium nucleatum induces premature and term stillbirths in pregnant mice: implication of oral bacteria in preterm birth. Infection and immunity, 72(4), 2272-2279.
Hanahan & Weinberg, (2011) Hallmarks of cancer: the next generation. cell, 144(5), 646-674.
Hardy et al., (1997) A lymphocyte-activating monoclonal antibody induces regression of human tumors in severe combined immunodeficient mice. Proceedings of the National Academy of Sciences, 94(11), 5756-5760.
Holliger et al., (1993) " Diabodies": small bivalent and bispecific antibody fragments. Proceedings of the National Academy of Sciences, 90(14), 6444-6448.
Hoogenboom & Winter, (1992) By-passing immunisation: human antibodies from synthetic repertoires of germline VH gene segments rearranged in vitro. Journal of molecular biology, 227(2), 381-388.
Huston et al., (1988) Protein engineering of antibody binding sites: recovery of specific activity in an anti-digoxin single-chain Fv analogue produced in *Escherichia coli*. Proceedings of the National Academy of Sciences, 85(16), 5879-5883.
Jakobovits et al., (1993) Analysis of homozygous mutant chimeric mice: deletion of the immunoglobulin heavy-chain joining region blocks B-cell development and antibody production. Proceedings of the National Academy of Sciences, 90(6), 2551-2555.
Jakobovits et al., (1993) Germ-line transmission and expression of a human-derived yeast artificial chromosome. Nature, 362(6417), 255-258.
Jobin, (2013) Colorectal cancer: looking for answers in the microbiota. Cancer discovery, 3(4), 384-387.
Johnston et al., (2014) The immunoreceptor TIGIT regulates anti-tumor and antiviral CD8+ T cell effector function. Cancer cell, 26(6), 923-937.
Jones et al., (1986) Replacing the complementarity-determining regions in a human antibody with those from a mouse. Nature, 321(6069), 522-525.
Khantasup et al., (2015) Design and Generation of Humanized Single-chain Fv Derived from Mouse Hybridoma for Potential Targeting Application. Monoclon Antib Immunodiagn Immunother 34(6): 404-417.
Koch et al., (2013) Activating natural cytotoxicity receptors of natural killer cells in cancer and infection. Trends in immunology, 34(4), 182-191.
Köhler & Milstein, (1975) Continuous cultures of fused cells secreting antibody of predefined specificity. Nature, 256 (5517), 495-497.
Kong et al., (2016) T-cell immunoglobulin and ITIM domain (TIGIT) associates with CD8+ T-cell exhaustion and poor clinical outcome in AML patients. Clinical Cancer Research, 22(12), 3057-3066.
Kostic et al., (2012) Genomic analysis identifies association of Fusobacterium with colorectal carcinoma. Genome research, 22(2), 292-298.
Kostic et al., (2013) Fusobacterium nucleatum potentiates intestinal tumorigenesis and modulates the tumor-immune microenvironment. Cell host & microbe, 14(2), 207-215.
Kühnel et al., (2004) The VASP tetramerization domain is a right-handed coiled coil based on a 15-residue repeat. Proceedings of the National Academy of Sciences of the United States of America, 101(49), 17027-17032.
Kurtulus et al., (2014) Mechanisms of TIGIT-driven immune suppression in cancer. Journal for immunotherapy of cancer, 2(S3), O13.
Lankry et al., (2010) Methods to identify and characterize different NK cell receptors and their ligands. In Natural Killer Cell Protocols, 249-273.
Lee & Tan, (2014) Fusobacterium nucleatum Activates the Immune Response through Retinoic Acid-Inducible Gene I. Journal of dental research, 93(2), 162-168.
Lefranc et al., (2003) IMGT unique numbering for immunoglobulin and T cell receptor variable domains and Ig superfamily V-like domains. Developmental & Comparative Immunology, 27(1), 55-77.
Liu et al., (2007) Fusobacterium nucleatum induces fetal death in mice via stimulation of TLR4-mediated placental Inflammatory response. The Journal of Immunology, 179(4), 2501-2508.
Liu et al., (2013) Recruitment of Grb2 and SHIP1 by the ITT-like motif of TIGIT suppresses granule polarization and cytotoxicity of NK cells. Cell death and differentiation, 20(3), 456-464.
Marks et al., (1991) By-passing immunization: human antibodies from V-gene libraries displayed on phage. Journal of molecular biology, 222(3), 581-597.
Marks et al., (1992) By-Passing Immunization: Building High Affinity Human Antibodies by Chain Shuffling. Nature Biotechnology, 10(7), 779-783.

* cited by examiner

ANTIBODIES SPECIFIC TO HUMAN T-CELL IMMUNOGLOBULIN AND ITIM DOMAIN (TIGIT)

CROSS-REFERENCE TO RELATED APPLICATIONS

This application is a divisional application of U.S. application Ser. No. 15/756,606, filed on Mar. 1, 2018, which is a 371 application of International Application No. PCT/IL2016/050952, filed on Sep. 1, 2016, which claims priority to U.S. Application No. 62/213,140, filed on Sep. 2, 2015, and U.S. Application No. 62/314,427, filed on Mar. 29, 2016, which is incorporated herein by reference.

SEQUENCE LISTING

The Sequence Listing submitted herewith is an ASCII text file (2021-02-05_Sequence_Listing.text, created on Feb. 4, 2021, 8970 bytes) via EFS-Web is hereby incorporated by reference.

FIELD OF THE INVENTION

The invention is in the field of immunotherapy and relates to monoclonal antibodies and fragments thereof which bind to the protein human TIGIT, to polynucleotide sequences encoding these antibodies and to hybridoma cells producing these antibodies. The invention further relates to therapeutic and diagnostic compositions comprising these antibodies and to methods of treating and diagnosing diseases, particularly cancer, using these monoclonal antibodies.

BACKGROUND OF THE INVENTION

Cancer immunotherapy is utilized for generating and augmenting an anti-tumor immune response, e.g., by treatment with antibodies specific to antigens on tumor cells, with cancer cells fused with antigen presenting cells (APC), or by specific activation of anti-tumor T cells.

Natural killer (NK) cells of the innate immune system play an important role in immune surveillance of tumors (Smyth et al., Nat Immunol. 2001. April; 2(4):293-9). NK cells kill MHC class I-deficient cells, tumors, viruses, parasites and bacteria directly and indirectly. NK cell activity is controlled by a balance of signals, delivered by inhibitory and activating NK cell receptors. There are several activating NK cell receptors that recognize various ligands, which can be stress-induced, self-molecules, viral components or tumor proteins (Koch et al., Trends in immunology 2013, 34, 182-191.; Seidel et al., Cellular and molecular life sciences, 2012). However, the exact mechanisms by which NK cells recognize and eliminate tumors via activating receptors are not well-understood, in part, because the tumor ligands of several activating NK cell receptors are unknown. In contrast, the identity of the ligands recognized by inhibitory NK cell receptors is well defined. NK cells express a vast repertoire of inhibitory receptors (Gardiner C. M., International journal of immunogenetics 2008, 35, 1-8.; Gonen-Gross et al., PloS one 2010, 5, e8941: Lankry et al., Methods in molecular biology 2010, 612, 249-273). Most of these inhibitory receptors belong to the KIR (Killer Inhibitory Receptors) family, recognizing both classical and non-classical major histocompatibility complex (MHC) class I proteins. KIRs are stochastically expressed on the NK cell surface, thus NK cells in a given individual express selected KIRs. NK cells also express additional inhibitory receptors that do not recognize MHC class I proteins, such as CEACAM1, CD300a and TIGIT (T-cell Immunoglobulin and ITIM Domain).

The human TIGIT protein is expressed on all NK cells, as well as on other immune cells such as T regulatory (Treg) CD8+ cells and Tumor infiltrating lymphocytes (Stanietsky et al., PNAS. 2009, 106, 17858-17863). It recognizes two very well defined ligands: poliovirus receptor (PVR, CD155) and Nectin2 (PVRL2/CD112) that are expressed on normal epithelia as well as over expressed on various tumor cells. The recognition of these ligands leads to the delivery of an inhibitory signal mediated by two motifs present in the cytoplasmatic tail of TIGIT: the immunoreceptor tail tyrosine (ITT)-like and the immunodominant tyrosine based inhibitory (ITIM) motifs (Liu et al., Cell death and differentiation 2013., 20, 456-464: Stanietsky et al., European journal of immunology, 2013. 43, 2138-2150). TIGIT, through its ITIM domain, inhibit NK cytotoxicity leading to immune evasion mechanism of tumor cells.

TIGIT expression on NK cells also serves as the receptor that binds the Fap2 protein of the anaerobic Gram-negative bacterium *Fusobacterium nucleatum* (*F. nucleatum*). The interaction between *F. Necleatum* and TIGIT leads to reduced NK cytotoxic activity. Fusobacteria are often enriched in patients with intestinal inflammation and cancer. It was suggested that *F. nucleatum* binding to TIGIT facilitates tumor evasion from NK associated cytotoxicity (Gur et al., Immunity. 2015 Feb. 17; 42(2): 344-355), providing an explanation on how bacteria found within tumors, in particular, *F. nucleatum*, promote tumor proliferation and enhance tumor progression (Jobin, Cancer discovery. 2013; 3:384-387; Sears and Garrett, Cell Host Microbe. 2014; 15:317-328).

Recently, it was shown that TIGIT and PD-1 impair tumor antigen-specific CD8+ T cells in melanoma patients (Chauvin el al. J Clin Invest. 2015; 125(5):2046-2058). In addition, TIGIT expression by CD8+ tumor-infiltrating lymphocytes (TILs) has been reported using gene expression analyses in a number of mouse and human solid tumors including lung, colon, breast, uterine, and renal cancers. Elevated TIGIT expression appears to correlate with CD8 and PD-1 expression. TIGIT expression on CD8+ TILs was observed in mouse tumors and in 3 human tumor samples, including non-small-cell lung and colon cancers (Johnston R J, et al. Cancer Cell. 2014; 26(6); 923-937).

It was suggested that TIGIT contributes to functional T-cell impairment and associates with poor clinical outcome in acute myeloid leukemia (AML). A study recently published by Kong et al. (Clin Cancer Res: 22(12); 3057-66), suggests that blockade of TIGIT to restore T-cell function and antitumor immunity may represent a novel effective leukemia therapeutic.

WO 2004/024068 describes agonists and antagonists to the molecule PRO52254, later identified as TIGIT, for treatment of autoimmune diseases and cancer without disclosing actual antibodies.

WO 2006/124667 discloses modulation of the protein zB7R1 (TIGIT) by monoclonal antibodies that block TIGIT binding to its ligand PVR. No binding affinities are provided.

WO 2009/126688 discloses TIGIT, and its ligand PVR, as targets for modulation of immune responses and suggests agonists and antagonists of these proteins for diagnosis and treatment of immune-related and inflammatory diseases.

WO 2015/009856 discloses combinations of programmed death 1 polypeptide (PD-1) antagonists and anti TIGIT antibodies for treatment of cancer and chronic infection.

WO 2016/028656 discloses anti-TIGIT antibodies, as well as use of these antibodies in the treatment of diseases such as cancer and infectious disease.

There is an unmet need to provide additional and more effective, specific, safe and/or stable agents that alone or in combination with other agents, allow cells of the immune system to attack tumor cells by inhibiting the suppresser activity of human TIGIT.

SUMMARY OF THE INVENTION

The present invention provides agents that recognize the immune cell inhibitory receptor "T-Cell immunoglobulin and ITIM domain" (TIGIT) and inhibit its suppressive activity on lymphocytes such as natural killer (NK) cells and T-cells. These agents are for example antibodies and fragment thereof, characterized by having unique sets of CDR sequences, exceptional high affinity and high specificity to human TIGIT and are useful in cancer immunotherapy for combating tumor immune evasion, as stand-alone therapy and in combination with other anti TIGIT antibodies and/or other anti-cancer agents.

Some of the monoclonal antibodies (mAbs) of the present invention exhibits absolute specificity to human TIGIT, as compared to mouse TIGIT for example, and affinity to the human TIGIT protein, which is higher than the affinity of the natural ligand, PVR (CD155) to human TIGIT. This makes these superior mAbs valuable candidates for use in cancer immune-therapy, enabling administration of lower doses with fewer side effects.

Some of the monoclonal antibodies of the present invention are capable not only to interfere with the binding of human TIGIT to its main ligand PVR (CD155) but also to inhibit, at least to some extent, the binding of TIGIT to at least one of its other ligands, such as CD112 and CD113.

Some of the anti-TIGIT monoclonal antibodies described herein have synergistic effect when combined with additional anti-cancer agents, such as other immunomodulatory proteins or receptor inhibitors. Non-limiting examples are mAbs specific to cytotoxic T-lymphocyte-associated protein 4 (CTLA-4, also known as CD152), and epidermal growth factor receptor inhibitors (EGFR).

The present invention provides, according to one aspect, an isolated antibody, or a fragment thereof comprising at least the antigen binding portion that recognizes human TIGIT with an affinity of at least $10^{-8}$M, and inhibits its interaction with at least one ligand.

According to some embodiments, the isolated antibody is a monoclonal antibody (mAb) or a fragment thereof.

According to some embodiments, the isolated monoclonal antibody or fragment comprises the complementarity determining region (CDR) sequences of a monoclonal antibody denoted VSIG9 #1 (or Vsig9.01), namely, the three CDR sequences contained in heavy chain variable region set forth in SEQ ID NO:7 and the three CDR sequences contained in light chain variable region set forth in SEQ ID NO:8. Determination of CDR sequences can be made according to any method known in the art, including but not limited to the methods known as KABAT, Chothia and IMGT. A selected set of CDRs may include sequences identified by more than one method, namely, some CDR sequences may be determined using KABAT and some using IMGT, for example.

According to some specific embodiments the isolated monoclonal antibody or fragment comprises heavy chain CDR1 ($^{HC}$CDR1) sequence comprising a sequence selected from the group consisting of: GYTFTSYGIS (SEQ ID NO:1), and TSYGIS (SEQ ID NO:11), heavy chain CDR2 ($^{HC}$CDR2) comprising the sequence: EIYPRSGNTYYNEKFKG (SEQ ID NO:2), heavy chain CDR3 ($^{HC}$CDR3) comprising the sequence: KGPYYTKNEDY (SEQ ID NO:3), light chain CDR1 ($^{LC}$CDR1) comprising the sequence: RASEHIYYSLA (SEQ ID NO:4), light chain CDR2 ($^{LC}$CDR2) comprising the sequence: NANSLED (SEQ ID NO:5), and light chain CDR3 ($^{LC}$CDR3) comprising the sequence: KQAYDVPRT (SEQ ID NO:6), and analogs thereof comprising no more than 5% amino acid substitution, deletion and/or insertion in the hypervariable region (HVR) sequence.

According to some specific embodiments the isolated monoclonal antibody or fragment comprises heavy chain CDR1 ($^{HC}$CDR1) sequence having the sequence GYTFTSYGIS (SEQ ID NO:1), heavy chain CDR2 ($^{HC}$CDR2) having the sequence: EIYPRSGNTYYNEKFKG (SEQ ID NO:2), heavy chain CDR3 ($^{HC}$CDR3) having the sequence: KGPYYTKNEDY (SEQ ID NO:3), light chain CDR1 ($^{LC}$CDR1) having the sequence: RASEHIYYSLA (SEQ ID NO:4), light chain CDR2 ($^{LC}$CDR2) having the sequence: NANSLED (SEQ ID NO:5), and light chain CDR3 ($^{LC}$CDR3) having the sequence: KQAYDVPRT (SEQ ID NO:6), and analogs thereof comprising no more than 5% amino acid substitution, deletion and/or insertion in the hypervariable region (HVR) sequence.

According to some embodiments, the isolated monoclonal antibody or fragment thereof comprises heavy chain variable region having the sequence: QVQLQESGAELARPGASVKLSCKASGYTFTSYGISWVKQRTGQGLEWIGEIYPRSG NTYYNEKFKGKATLTADKSSSTAYMELSSLTSEDSAVYFCARKGPYYTKNEDYWG QGTILTVSS (SEQ ID NO:7), or an analog or derivative thereof having at least 90% sequence identity with the heavy chain variable region sequence.

According to some embodiments, the isolated monoclonal antibody or fragment thereof comprises light chain variable region having the sequence: DIQMTQSPASLAASVGETVTITCRASEHIYYSLAWYQQKQGKSPQLLIYNANSLED GVPSRFSGSGSGTQYSMKINSMQPEDTATYFCKQAYDVPRT FGGGTKLEIKRADAAPTVS (SEQ ID NO:8), or an analog thereof having at least 90% sequence identity with the light chain variable region sequence.

According to a specific embodiment, the isolated monoclonal antibody or fragment thereof comprises a heavy chain variable region having the sequence: QVQLQESGAELARPGASVKLSCKASGYTFTSYGISWVKQRTGQGLEWIGEIYPRSG NTYYNEKFKGKATLTADKSSSTAYMELSSLTSEDSAVYFCARKGPYYTKNEDYWG QGTILTVSS (SEQ ID NO:7), and a light chain variable region having the sequence: DIQMTQSPASLAASVGETVTITCRASEHIYYSLAWYQQKQGKSPQLLIYNANSLED GVPSRFSGSGSGTQYSMKINSMQPEDTATYFCKQAYDVPRTFGGGTKLEIKRADAA PTVS (SEQ ID NO:8), or an analog thereof having at least 90% sequence identity with the light and/or heavy chain sequence.

The invention also encompasses antibody or antibody fragment capable of binding with high affinity to an epitope within the human TIGIT protein to which mAb VSIG9 #1 binds.

According to other embodiments, the isolated monoclonal antibody comprises the complementarity determining region (CDR) sequences of a monoclonal antibody denoted #4 (or 258-cs1 #4), namely, the three CDR sequences contained in heavy chain variable region set forth in SEQ ID NO:18 and the three CDR sequences contained in light chain variable region set forth in SEQ ID NO:19.

According to some specific embodiments the isolated monoclonal antibody comprises heavy chain CDR1 ($^{HC}$CDR1) comprising the sequence IYCIH (SEQ ID NO:12), heavy chain CDR2 ($^{HC}$CDR2) comprising the sequence: EISPSNGRTIYNEKFKN (SEQ ID NO:13), heavy chain CDR3 ($^{HC}$CDR3) comprising the sequence: SDGYDGYYFDY (SEQ ID NO:14), light chain CDR1 ($^{LC}$CDR1) comprising the sequence: RASQEISGYLN (SEQ ID NO:15), light chain CDR2 ($^{LC}$CDR2) comprising the sequence: AASTLDS (SEQ ID NO:16), and light chain CDR3 ($^{LC}$CDR3) comprising the sequence: LQYASYPRT (SEQ ID NO:17), and analogs thereof comprising no more than 5% amino acid substitution, deletion and/or insertion in the hypervariable region (HVR) sequence.

According to some specific embodiments the isolated monoclonal antibody comprises heavy chain CDR1 ($^{HC}$CDR1) having the sequence IYCIH (SEQ ID NO: 12), heavy chain CDR2 ($^{HC}$CDR2) having the sequence: EISPSNGRTIYNEKFKN (SEQ ID NO:13), heavy chain CDR3 ($^{HC}$CDR3) having the sequence: SDGYDGYYFDY (SEQ ID NO:14), light chain CDR1 ($^{LC}$CDR1) having the sequence: RASQEISGYLN (SEQ ID NO: 15), light chain CDR2 ($^{LC}$CDR2) having the sequence: AASTLDS (SEQ ID NO:16), and light chain CDR3 ($^{LC}$CDR3) having the sequence: LQYASYPRT (SEQ ID NO:17), and analogs and derivative thereof.

According to some embodiments, the isolated monoclonal antibody or fragment thereof comprises heavy chain variable region having the sequence: QVQLLQPGAELVKP-GASVKLSCKASGYTFTIYCIHWVKQRPGQ-GLEWIGEISPSNG RTIYNEKFKNKATLTIDKSST-TAYMQLSSLTSEDSAVYCCAISDGYDGYYFDYWGQ GTTLTVSS (SEQ ID NO:18), or an analog or derivative thereof having at least 90% sequence identity with the heavy chain sequence.

According to some embodiments, the isolated monoclonal antibody or fragment thereof comprises light chain variable region having the sequence: DIQMTQSPSSL-SASLGERVSLTCRASQEISGYLNWLQQKPDGTIKRLI-YAASTLDSG VPKRFSGSRSGSDYSLTISRLESED-FADYYCLQYASYPRTFGGGTKLEIK (SEQ ID NO:19), or an analog or derivative thereof having at least 90% sequence identity with the light chain sequence.

The invention also encompasses antibody or antibody fragment capable of binding with high affinity to an epitope within the human TIGIT protein to which mAb #4 binds.

Analogs and derivatives of the isolated mAb antibodies, and the antibody fragments described above, are also within the scope of the invention. In particular analogs or isolated mAbs or fragment thereof comprising at least one variable region set forth in a sequence selected from the group consisting of: SEQ ID No: 7, 8, 18 and 19 are also within the scope of the present invention.

According to some embodiments, the antibody or antibody fragment analog have at least 95% sequence identity with the hypervariable region of the reference antibody sequence, or at least 90% sequence identity with the heavy or light chain variable regions of the reference antibody.

According to certain embodiments, the analog or derivative of the isolated antibody or fragment thereof has at least 91, 92, 93, 94, 95, 96, 97, 98 or 99% sequence identity with a variable region of the reference antibody sequence. Each possibility represents a separate embodiment of the invention.

According to another aspect the present invention provides a monoclonal antibody or an antibody fragment that recognizes TIGIT, comprising an antigen binding domain (ABD) comprising three CDRs of a light chain and three CDRs of a heavy chain, wherein said CDRs have at least 90% sequence identity or similarity with the CDRs of the ABD of: (i) a monoclonal mouse antibody (herein identified as VSIG9 #1 or Vsig9.01 clone) comprising a heavy chain variable region of SEQ ID NO:7 and a light chain variable region of SEQ ID NO:8; or (ii) a monoclonal mouse antibody (herein identified #4 or 258-CS1 #4 clone) comprising a heavy chain variable region of SEQ ID NO:18 and a light chain variable region of SEQ ID NO: 19. According to some embodiments, the CDRs have at least 91%, at least 92%, at least 93% or at least 94% sequence identity or similarity with those of VSIG9 #1 or 258-CS1 #4. According to other embodiments, the ABD has at least 95%, at least 96%, or at least 97%, at least 98% or at least 99% sequence identity or similarity with VSIG9 #1 or 258-CS1 #4.

According to some embodiments, the antibody or antibody fragment according to the invention comprises a heavy chain variable region set forth in SEQ ID NO:7, or an analog having at least 95% sequence similarity with said sequence. According to other embodiments, the antibody or antibody fragment according to the invention comprises a heavy chain variable region set forth in SEQ ID NO:18, or an analog having at least 95% sequence similarity with said sequence.

According to some embodiments, the antibody or antibody fragment comprises a light chain variable region set forth in SEQ ID NO:8, or an analog having at least 95% sequence similarity with said sequence. According to other embodiments, the antibody or antibody fragment comprises a light chain variable region set forth in SEQ ID NO:19, or an analog having at least 95% sequence similarity with said sequence.

According to some embodiments, the antibody or antibody fragment comprises a heavy chain and a light chain, wherein: (i) the heavy chain comprises SEQ ID NO:7 and the light chain comprises SEQ ID NO8; or (ii) the heavy chain comprises SEQ ID NO: 18 and the light chain comprises SEQ ID NO: 19. Analogs of the antibodies or fragments, having at least 95% sequence similarity with said heavy or light chains are also included.

According to some embodiments, the analog has at least 96, 97, 98 or 99% sequence identity with an antibody light or heavy chain variable regions described above. According to some embodiments, the analog comprises no more than one amino acid substitution, deletion or addition to one or more CDR sequences of the hypervariable region, namely, any one of the CDR sequences set forth in SEQ ID Nos: 1-6 and 12-17. According to some embodiments, the amino acid substitution is a conservative substitution. Each possibility represents a separate embodiment of the present invention.

According to some embodiments, the antibody or antibody fragment comprises a hypervariable region (HVR) having light and heavy chain regions defined above, in which 1, 2, 3, 4, or 5 amino acids were substituted, deleted and/or added. Each possibility represents a separate embodiment of the invention. According to specific embodiments, the antibody or antibody fragment comprises a hypervariable region having a set of CDR sequences selected from SEQ ID NOs.: 1-6 and 12-17, in which no more than one amino acid is substituted, deleted or added to at least one CDR sequence. According to some embodiments, the amino acid substitution is a conservative substitution. Each possibility represents a separate embodiment of the present invention.

According to some embodiments, the antibody or antibody fragment is capable of recognizing TIGIT protein expressed on T-cells.

According to some embodiments, the antibody or antibody fragment is capable of recognizing human TIGIT protein expressed on dendritic or NK cells.

According to some embodiments, the antibody or antibody fragment is capable of recognizing human TIGIT protein expressed on T-regulatory cells (Treg).

According to some embodiments, the antibody or antibody fragment is capable of recognizing human TIGIT protein expressed on CD8+ tumor infiltrating lymphocytes (TILs).

According to some embodiments, the antibody or antibody fragment is capable of inhibiting human TIGIT binding to a ligand expressed on T-cells.

According to some embodiments, the antibody or antibody fragment is capable of inhibiting human TIGIT binding to ligand expressed on dendritic or NK cells.

According to yet other embodiments, the antibody or antibody fragment is capable of inhibiting human TIGIT binding to ligand expressed on tumor cells.

According to some embodiments, the antibody or antibody fragment is capable of inhibiting binding of human TIGIT to a ligand selected from the group consisting of: PVR (CD155), PVRL2 (CD112/Nectin2), PVRL3 (CD113) and any combination thereof.

According to some embodiments, the isolated antibody or fragment thereof binds to human TIGIT protein with a dissociation constant (Kd) of at least about 50 nM. According to some embodiments the isolated antibody or fragment thereof binds to human TIGIT protein with a binding affinity of at least 1 nM. Thus, according to some embodiments, antibody or antibody according to the inventor has an affinity to human TIGIT of at least about $5 \times 10^{-8}$M. According to other embodiments, an antibody or antibody fragment binds with an affinity of $10^{-8}$M, $5 \times 10^{-9}$M, $10^{-9}$M, $5 \times 10^{-10}$M, $10^{-10}$M, $5 \times 10^{-11}$M, $10^{-11}$M or even higher to human TIGIT. Each possibility represents a separate embodiment of the invention.

According to a specific embodiment, the mAb is selected from the group consisting of: non-human antibody, humanized antibody, human antibody, chimeric antibody, bispecific antibody and an antibody fragment comprising at least the antigen-binding portion of an antibody. According to a specific embodiment, the antibody fragment is selected from the group consisting of: Fab, Fab', F(ab')2, Fd, Fd', Fv, dAb, isolated CDR region, single chain antibody (scab), "diabodies", and "linear antibodies". Each possibility represents a separate embodiment of the present invention.

According to some embodiments, the antibody is a bispecific antibody or bispecific antibody fragment, capable of binding to two different epitopes or antigens.

According to some embodiments, a bispecific mAb or bispecific mAb fragment comprises two different hyper variable regions (HVR), each comprising a different set of CDR sequences.

According to some embodiments the bispecific mAb or fragment comprises the binding domains of two different anti-TIGIT antibodies. Each HVR of a bispecific mAb or fragment according to these embodiments is cable of binding to a different epitope of the human TIGIT protein.

According to some embodiments, one HVR of a bispecific mAb or fragment comprises the CDRs contained in heavy chain sequence set forth in SEQ ID NO: 7 and light chain sequence set for the in SEQ ID NO:8 of the monoclonal antibody VSIG9 #1; and the second HVR comprises the CDRs contained in heavy chain sequence set for the in SEQ ID NO:18 and light chain sequence set forth in SEQ ID NO: 19 of the monoclonal antibody #4 (or 258-cs1 #4).

According to some embodiments, one HVR of a bispecific mAb or fragment thereof comprises the CDRs: SEQ ID NO: 1 or SEQ ID NO: 11, SEQ ID NO:2, SEQ ID NO:3, SEQ ID NO:4, SEQ ID NO:5 and SEQ ID NO:6; and the second HVR comprises the CDRs: SEQ ID NO: 12, SEQ ID NO: 13, SEQ ID NO: 14, SEQ ID NO: 15, SEQ ID NO: 16 and SEQ ID NO:17.

According to other embodiments, one HVR of a bispecific antibody or bispecific antibody fragment according to the invention binds to human TIGIT and the second HVR binds to another protein, such as a protein involved in immune regulation or a tumor antigen. According to some specific embodiments, the second HVR of the bispecific antibody binds a checkpoint molecule.

According to some embodiments, the antibody or antibody fragment comprises a framework sequence selected from the group consisting of: mouse IgG2a, mouse IgG2b, mouse IgG3, human IgG1, human IgG2, human IgG3, and human IgG4. Each possibility represents a separate embodiment of the present invention.

According to other embodiments, the antibody is a humanized antibody or the antibody fragment is a fragment of a humanized antibody.

According to some embodiments, the humanized antibody or antibody fragment comprises a framework sequence selected from the group consisting of: human IgG1, human IgG2, human IgG3, and human IgG4. Each possibility represents a separate embodiment of the present invention.

According to yet other embodiments, an antibody conjugate comprising at least one antibody or antibody fragment that recognizes TIGIT and inhibits binding to its ligand is provided wherein said antibody or antibody fragment comprises the complementarity determining regions (CDRs) sequences: (i) heavy chain CDR1 having a sequence selected from: GYTFTSYGIS (SEQ ID NO:1), and TSYGIS (SEQ ID NO:11), heavy chain CDR2 having the sequence: EIYPRSGNTYYNEKFKG (SEQ ID NO:2), heavy chain CDR3 having the sequence: KGPYYTKNEDY (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); or (ii) heavy chain CDR1 having the sequence IYCIH (SEQ ID NO:12), heavy chain CDR2 having the sequence: EISPSNGRTIYNEKFKN (SEQ ID NO: 13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO:16), and light chain CDR3 having the sequence: LQYASYPRT (SEQ ID NO: 17).

According to some embodiments, the conjugate comprises a carrier protein.

Polynucleotide sequences encoding monoclonal antibodies, having high affinity and specificity for TIGIT, as well as vectors and host cells carrying these polynucleotide sequences, are provided according to another aspect of the present invention.

According to some embodiments, the polynucleotide sequence encodes an antibody or antibody fragment or chain capable of binding to an epitope within the human TIGIT protein to which binds: (i) a mouse monoclonal antibody (herein identified as VSIG9 #1) having a heavy chain variable region of SEQ ID NO:7 and a light chain variable region of SEQ ID NO:8; or (ii) a mouse monoclonal antibody (herein identified as 258-CS1 #4) having a heavy chain variable region of SEQ ID NO: 18 and a light chain variable region of SEQ ID NO:19.

According to some embodiments, the polynucleotide sequence encodes an antibody or antibody fragment or chain comprising the sequence set forth in SEQ ID NO:7. According to some embodiments, the polynucleotide sequence encodes an antibody or antibody fragment or chain comprising the sequence set forth in SEQ ID NO:8.

According to other embodiments, the polynucleotide sequence encodes an antibody or antibody fragment or chain comprising the sequence set forth in SEQ ID NO: 18. According to additional embodiments, the polynucleotide sequence encodes an antibody or antibody fragment or chain comprising the sequence set forth in SEQ ID NO: 19.

According to yet some embodiments, a polynucleotide sequence according to the invention encodes an antibody or antibody fragment or chain comprising the six CDR sequences: (i) heavy chain CDR1 sequence selected from: GYTFTSYGIS (SEQ ID NO:1), and TSYGIS (SEQ ID NO:11), heavy chain CDR2 having the sequence: EIYPRSGNTYYNEKFKG (SEQ ID NO:2), heavy chain CDR3 having the sequence: KGPYYTKNEDY (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); or (ii) heavy chain CDR1 having the sequence IYCIH (SEQ ID NO: 12), heavy chain CDR2 having the sequence: EISPSNGRTIYNEKFKN (SEQ ID NO: 13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO:16), and light chain CDR3 having the sequence: LQYASYPRT (SEQ ID NO:17).

According to some embodiments, a polynucleotide sequences defined above encodes a molecule selected from the group consisting of: an antibody an antibody fragment comprising at least an antigen-binding portion, an antibody conjugate comprising said antibody or antibody fragment, and a bispecific antibody. Each possibility represents a separate embodiment of the present invention.

According to some embodiments, a polynucleotide sequence is provided comprising the sequence of a monoclonal antibody heavy chain variable region set forth in SEQ ID NO:9, or a variant thereof having at least 90% sequence identity:

```
                                          (SEQ ID NO: 9)
CAGGTGCAGCTGCAGGAGTCTGGAGCTGAGCTGGCGAGGCCTGGGGCTTC

AGTGAAGCTGTCCTGCAAGGCTTCTGGCTACACCTTCACAAGCTATGGTA

TAAGCTGGGTGAAGCAGAGAACTGGACAGGGCCTTGAGTGGATTGGAGAG

ATTTATCCCAGAAGTGGTAATACTTACTACAATGAGAAGTTCAAGGGCAA

GGCCACACTGACTGCAGACAAATCCTCCAGCACAGCGTACATGGAGCTCA

GCAGCCTGACATCTGAGGACTCTGCGGTCTATTTCTGTGCAAGAAAGGGA

CCCTACTATACTAAGAACGAGGACTACTGGGGCCAAGGCACCATTCTCAC

AGTCTCCTCA.
```

According to some embodiments, a polynucleotide sequence is provided comprising the sequence of a monoclonal antibody heavy chain variable region set forth in SEQ ID NO:20, or a variant thereof having at least 90% sequence identity:

```
                                         (SEQ ID NO: 20)
CAGGTCCAACTGCTGCAGCCTGGGGCTGAACTGGTGAAGCCTGGGGCTTC

AGTGAAGCTGTCCTGCAAGGCTTCTGGCTACACCTTCACCATCTACTGTA

TACACTGGGTGAAGCAGAGGCCTGGACAAGGCCTTGAGTGGATTGGAGAG

ATTAGTCCTAGCAACGGTCGTACTATCTACAATGAGAAGTTCAAGAACAA

GGCCACACTGACTATAGACAAATCCTCCACCACAGCCTACATGCAACTCA

GCAGCCTGACATCTGAGGACTCTGCGGTCTATTGCTGTGCAATATCGGAT

GGTTACGACGGATACTACTTTGACTACTGGGGCCAAGGCACCACTCTCAC

AGTCTCCTCA.
```

According to some embodiments, a polynucleotide sequence is provided comprising the sequence of a monoclonal antibody light chain variable region set forth in SEQ ID NO:10, or a variant thereof having at least 90% sequence identity:

```
                                         (SEQ ID NO: 10)
GACATCCAGATGACTCAGTCTCCAGCCTCCCTGGCTGCATCTGTGGGAGA

AACTGTCACCATCACATGTCGAGCAAGTGAGCACATTTACTACAGTTTAG

CATGGTATCAGCAGAAGCAAGGGAAATCTCCTCAGCTCCTGATCTATAAT

GCAAACAGCTTGGAAGATGGTGTCCCATCGAGGTTCAGTGGCAGTGGATC

TGGGACACAATATTCTATGAAGATCAACAGCATGCAGCCTGAAGATACCG

CAACTTATTTCTGTAAACAGGCTTATGACGTTCCTCGGACCTTCGGTGGA

GGCACCAAGCTGGAAATCAAACGGG CTGATGCTGCACCAACTGTATCC.
```

According to some embodiments, a polynucleotide sequence is provided comprising the sequence of a monoclonal antibody light chain variable region set forth in SEQ ID NO:21, or a variant thereof having at least 90% sequence identity:

```
                                         (SEQ ID NO: 21)
GACATCCAGATGACCCAGTCTCCATCCTCCTTATCTGCCTCTCTGGGAGA

AAGAGTCAGTCTCACTTGTCGGGCAAGTCAGGAAATTAGTGGTTACTTAA

ACTGGCTTCAGCAGAAACCAGATGGAACTATTAAACGCCTGATCTACGCC

GCATCCACTTTAGATTCTGGTGTCCCAAAAAGGTTCAGTGGCAGTAGGTC

TGGGTCAGATTATTCTCTCACCATCAGCAGACTTGAGTCTGAAGATTTTG

CAGACTATTACTGTCTACAATATGCTAGTTATCCTCGGACGTTCGGTGGA

GGCACCAAGCTGGAAATCAAA.
```

The present invention provides, according to some embodiments, a polypeptide comprising at least one sequence encoded by at least one polynucleotide sequence disclosed above.

In a further aspect the present invention provides a nucleic acid construct comprising a nucleic acid molecule encoding at least one antibody chain or fragment thereof according to the present invention. According to some embodiments the nucleic acid construct is a plasmid.

According to some embodiments the plasmid comprises a polynucleotide sequence set forth in SEQ ID NO:9 or SEQ ID NO:20.

According to other embodiments the plasmid comprises a polynucleotide sequence set forth in SEQ ID NO: 10 or SEQ ID NO:21.

In still another aspect the present invention provides a hybridoma cell capable of producing an antibody or an antibody fragment comprising the specific CDR sequences and/or specific heavy and light chain variable regions defined above.

According to some embodiments, a hybridoma cell is provided comprising at least one polynucleotide sequence disclosed above.

According to some embodiments, the hybridoma is a cable of producing a monoclonal antibody comprising the six complementarity determining regions (CDRs) sequences: (i) heavy chain CDR1 sequence selected from GYTFTSYGIS (SEQ ID NO:1) and TSYGIS (SEQ ID NO:11), heavy chain CDR2 having the sequence: EIY-PRSGNTYYNEKFKG (SEQ ID NO:2), heavy chain CDR3 having the sequence: KGPYYTKNEDY (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); or (ii) heavy chain CDR1 having the sequence IYCIH (SEQ ID NO:12), heavy chain CDR2 having the sequence: EISPSN-GRTIYNEKFKN (SEQ ID NO:13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO:16), and light chain CDR3 having the sequence: LQYASYPRT (SEQ ID NO:17).

Antibodies or fragments thereof according to the present invention may be attached to a cytotoxic moiety, a radioactive moiety, or an identifiable moiety.

The present invention provides, according to another aspect, a pharmaceutical composition comprising as an active ingredient, at least one antibody, antibody fragment or conjugates thereof, that recognizes TIGIT with high affinity and specificity and inhibits its interaction with one of its ligands, and optionally at least one pharmaceutical acceptable excipient, diluent, salt or carrier.

According to some embodiments, the pharmaceutical composition comprises a monoclonal antibody or a fragment thereof which is capable of binding to an epitope within the human TIGIT protein to which binds a mouse monoclonal antibody selected from the group consisting of: (i) an antibody (herein identified as VSIG9 #1 or Vsig9.01) having a heavy chain variable region of SEQ ID NO:7 and a light chain variable region of SEQ ID NO:8; and (ii) an antibody (herein identified as #4 or 258-CS1 #4) having a heavy chain variable region of SEQ ID NO:18 and a light chain variable region of SEQ ID NO:19.

According to some embodiments, the monoclonal antibody or antibody fragment thereof comprises the six CDRs: (i) heavy chain CDR1 sequence selected from: GYTFTSY-GIS (SEQ ID NO:1), and TSYGIS (SEQ ID NO:11), heavy chain CDR2 having the sequence: EIYPRSGN-TYYNEKFKG (SEQ ID NO:2), heavy chain CDR3 having the sequence: KGPYYTKNEDY(SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); or (ii) heavy chain CDR1 having the sequence IYCIH (SEQ ID NO:12), heavy chain CDR2 having the sequence: EISPSNGRTIYNEKFKN (SEQ ID NO:13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO:16), and light chain CDR3 having the sequence: LQYASYPRT (SEQ ID NO:17).

According to some embodiments, the pharmaceutical composition comprises a monoclonal antibody or fragment thereof comprising a heavy chain variable region having the sequence: (i)

(i)
(SEQ ID NO: 7)
QVQLQESGAELARPGASVKLSCKASGYTFTSYGISWVKQRTGQGLEWIGE

IYPRSGNTYYNEKFKGKATLTADKSSSTAYMELSSLTSEDSAVYFCARKG

PYYTKNEDYWGQGTILTVSS;
or (ii)
(SEQ ID NO: 18)
QVQLLQPGAELVKPGASVKLSCKASGYTFTIYCIHWVKQRPGQGLEWIGE

ISPSNGRTIYNEKFKNKATLTIDKSSTTAYMQLSSLTSEDSAVYCCAISD

GYDGYYFDYWGQGTTLTVSS.

According to some embodiments, the pharmaceutical composition comprises a monoclonal antibody or fragment thereof comprising a light chain variable region having the sequence: (i)

(i)
(SEQ ID NO: 8)
DIQMTQSPASLAASVGETVTITCRASEHIYYSLA

WYQQKQGKSPQLLIYNANSLEDGVPSRFSGSGSGTQYSMKINSMQPEDT

ATYFCKQAYDVPRT FGGGTKLEIKRADAAPTVS;
or (ii)
(SEQ ID NO: 19)
DIQMTQSPSSLSASLGERVSLTCRASQEISGYLNWLQQKPDGTIKRLIY

AASTLDSGVPKRFSGSRSGSDYSLTISRLESEDFADYYCLQYASYPRTF

GGGTKLEIK.

According to a specific embodiment, the pharmaceutical composition comprises a monoclonal antibody or fragment thereof comprising a heavy chain variable region having the sequence:

(SEQ ID NO: 7)
QVQLQESGAELARPGASVKLSCKASGYTFTSYGISWVKQRTGQGLEWIG

EIYPRSGNTYYNEKFKGKATLTADKSSSTAYMELSSLTSEDSAVYFCAR

KGPYYTKNEDYWGQGTILTVSS, and a light chain variable region having the sequence:

(SEQ ID NO: 8)
DIQMTQSPASLAASVGETVTITCRASEHIYYSLA

WYQQKQGKSPQLLIYNANSLEDGVPSRFSGSGSGTQYSMKINSMQPEDT

ATYFCKQAYDVPRT FGGGTKLEIKRADAAPTVS.

According to an additional specific embodiment, the pharmaceutical composition comprises a monoclonal antibody or fragment thereof comprising a heavy chain variable region having the sequence:

(SEQ ID NO: 18)
QVQLLQPGAELVKPGASVKLSCKASGYTFTIYCIHWVKQRPGQGLEWIG

ISPSNGRTIYNEKFKNKATLTIDKSSTTAYMQLSSLTSED

SAVYCCAISDGYDGYYFDYWGQGTTLTVSS and a light chain variable region having the sequence:

(SEQ ID NO: 19)
DIQMTQSPSSLSASLGERVSLTCRASQEISGYLNWLQQKPDGTIKRLIY

AASTLDSGVPKRFSGSRSGSDYSLTISRLESEDFADYYCLQYASYPRTF

GGGTKLEIK.

According to some embodiments, the pharmaceutical composition comprises at least one bispecific antibody comprising two different HVR regions, wherein at least one of the HVR binds with high affinity and selectivity to human TIGIT.

According to some embodiments, the second HVR binds to another epitope on human TIGIT or to a different antigen.

According to some embodiments, one HVR comprises the CDR sequences of the antibody denoted VSIG9 #1 (or Vsig9.01) and the second HVR comprises the CDR sequences of the antibody denoted 258-cs1 #4 (also denoted #4).

According to some embodiments, one HVR comprises the six CDR sequences of the antibody denoted VSIG9 #1 or the six CDRs the antibody denoted 258-cs1 #4, and the second HVR comprises six different CDRs capable of binding human TIGIT or a different antigen.

According to some embodiments, the pharmaceutical composition comprises a combination of at least two antibodies, or antibody fragments, which recognizes human TIGIT, wherein at least one of the antibodies has high affinity and selectivity to human TIGIT. According to some embodiments, the at least one antibody or antibody fragment that has high affinity and selectivity to human TIGIT comprises the CDR sequences of the antibody denoted VSIG9 #1 (or Vsig9.01) or 258-cs1 #4 (also denoted #4).

According to some specific embodiments, one monoclonal antibody or antibody fragment comprises the CDR sequences of the antibody denoted VSIG9 #1 and the second antibody or antibody fragment comprises the CDR sequences of the antibody denoted 258-cs1 #4 (or #4).

According to yet other embodiments, the composition comprises one mAb or fragment that specifically binds TIGIT, according to the invention, and one mAb or fragment that specifically binds a different antigen, such as, cell-receptor, tumor antigen or immunomodulatory.

Also provided are pharmaceutical compositions, comprising at least one antibody, antibody fragment or antibody conjugate according to the invention, for use in restoring NK cytotoxicity by inhibiting binding of TIGIT ligand to NK cells.

According to some embodiments, the pharmaceutical composition according to the present invention is for use in cancer immunotherapy or in enhancing immune response.

According to yet another aspect, the present invention provides a method of inhibiting binding of human TIGIT to at least one ligand by using a monoclonal antibody or antibody fragment defined above.

According to some embodiments, the antibody or antibody fragment is capable of inhibiting binding of TIGIT to a ligand selected from the group consisting of: PVR (CD155), PVRL2 (CD112), PVRL3 (CD113), and any combination thereof.

According to some embodiments, a method of restoring NK cytotoxicity is provided by inhibiting binding of TIGIT to at least one ligand expressed on NK cells, comprising administering to a subject in need thereof a pharmaceutical composition comprising at least one antibody, antibody fragment or antibody conjugate that recognizes human TIGIT with high affinity and specificity.

According to some embodiments, the antibody, antibody fragment or antibody conjugate is capable of inhibiting human TIGIT binding to a ligand expressed on T-cells.

According to some embodiments, the antibody, antibody fragment or antibody conjugate is capable of inhibiting human TIGIT binding to a ligand expressed on dendritic or NK cells.

According to yet other embodiments, the antibody, antibody fragment or antibody conjugate is capable of inhibiting human TIGIT binding to ligand expressed on tumor cells.

The invention provides in another aspect methods for enhancing immune response in a subject in need thereof comprising administering to said subject a therapeutically effective amount of a monoclonal antibody, antibody fragment or antibody conjugate defined above.

According to yet another aspect, the present invention provides a method of treating cancer comprising administering to a subject in need thereof, a pharmaceutical composition comprising at least one antibody, antibody fragment or conjugate thereof, that recognizes human TIGIT with high affinity and specificity and capable of inhibiting its binding to its ligand.

According to some embodiments, the cancer is selected from the group consisting of: lung, thyroid, breast, colon, melanoma, prostate, hepatic, bladder, renal, cervical, pancreatic, leukemia, lymphoma, myeloid, ovarian, uterus, sarcoma, biliary, non-small-cell lung and endometrial cells cancer. Each possibility represents a separate embodiment of the invention.

According to some embodiments, the cancer is selected from the group consisting of: melanoma, breast cancer, non-small-cell lung and colon and hepatic (liver) cancer. Each possibility represents a separate embodiment of the invention.

According to some specific embodiments, the cancer is melanoma.

According to some embodiments, the cancer is a solid cancer. According to some specific embodiments, the solid cancer is selected from the group consisting of melanoma (skin), lung, colon, breast, uterine, and renal cancer.

According to some embodiments, the cancer is leukemia. According to some specific embodiments, the cancer is acute myeloid leukemia (AML).

According to some embodiments, the antibody in the pharmaceutical composition administered is selected from the group consisting of: (i) a monoclonal antibody comprising the CDR sequences contained in heavy chain variable region set forth in SEQ ID NO:7 and the CDR sequences contained in light chain variable region set forth in SEQ ID NO:8; or (ii) a monoclonal antibody comprising the CDR sequences contained in heavy chain variable region set forth in SEQ ID NO:18 and the CDR sequences contained in light chain variable region set forth in SEQ ID NO: 19.

According to some specific embodiments, the monoclonal antibody in the pharmaceutical composition administered comprises: heavy chain CDR1 having the sequence: GYTFTSYGIS (SEQ ID NO:1), heavy chain CDR2 having the sequence: EIYPRSGNTYYNEKFKG (SEQ ID NO:2), heavy chain CDR3 having the sequence: KGPYYTKNEDY (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6).

According to other specific embodiments, the monoclonal antibody in the pharmaceutical composition administered comprises: heavy chain CDR1 having the sequence IYCIH (SEQ ID NO:12), heavy chain CDR2 having the sequence: EISPSNGRTIYNEKFKN (SEQ ID NO:13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO:16), and light chain CDR3 having the sequence: LQYASYPRT (SEQ ID NO:17).

According to some embodiments, the method of treating cancer comprises administering or performing at least one additional anti cancer therapy. According to certain embodiments, the additional anticancer therapy is surgery, chemotherapy, radiotherapy, or immunotherapy.

According to some embodiments, the method of treating cancer comprises administration of a monoclonal antibody that recognizes human TIGIT with high affinity and specificity and an additional anti-cancer agent. According to some embodiments, the additional anti-cancer agent is selected from the group consisting of: immune-modulator, activated lymphocyte cell, kinase inhibitor and chemotherapeutic agent.

According to some embodiments, the additional immune-modulator is an antibody, antibody fragment or antibody conjugate that binds to a different epitope on human TIGIT to which the monoclonal antibody denoted VSIG9 #1 (or Vsig9.01) binds.

According to other embodiments, the additional immune-modulator is an antibody, antibody fragment or antibody conjugate that binds to an antigen other than human TIGIT.

According to some embodiments, the additional immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), and any combination thereof. Each possibility represents a separate embodiment of the invention.

According to some embodiments, the method of treating cancer comprises administration of a pharmaceutical composition comprising a monoclonal antibody that recognizes human TIGIT according to the invention and an anti-PD-1 antibody.

According to some embodiments, the method of treating cancer comprises administration of a pharmaceutical composition comprising a monoclonal antibody that recognizes human TIGIT according to the invention and an anti-CTLA-4 antibody.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of: Erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and combinations thereof. Each possibility represents a separate embodiment of the invention.

According to some embodiments, the anti-cancer agent is epidermal growth factor receptor (EGFR) inhibitor. According to some embodiments, the EGFR inhibitor is selected from the group consisting of: Cetuximab (Erbitux®), Panitumumab (Vectibix®), and necitumumab (Portrazza®). According to some embodiments, the EGFR inhibitor is Cetuximab (Erbitux®).

The present invention thus provides a method of increasing or stimulating an immune response by administering a pharmaceutical composition comprising at least one antibody, conjugate, or fragment thereof that recognizes TIGIT and inhibits its binding to its ligand.

The present invention further comprises, according to another aspect, a method of determining or quantifying the expression of TIGIT, the method comprising contacting a biological sample with an antibody or antibody fragment, and measuring the level of complex formation, wherein the antibody or antibody fragment comprises the complementarity determining regions (CDRs) selected from the group consisting of: (i) heavy chain CDR1 having the sequence: GYTFTSYGIS (SEQ ID NO:1), heavy chain CDR2 having the sequence: EIYPRSGNTYYNEKFKG (SEQ ID NO:2), heavy chain CDR3 having the sequence: KGPYYTKNEDYV (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); and (ii) heavy chain CDR1 having the sequence IYCIH (SEQ ID NO:12), heavy chain CDR2 having the sequence: EISPSNGRTIYNEKFKN (SEQ ID NO:13), heavy chain CDR3 having the sequence: SDGYDGYYFDY (SEQ ID NO:14), light chain CDR1 having the sequence: RASQEISGYLN (SEQ ID NO:15), light chain CDR2 having the sequence: AASTLDS (SEQ ID NO: 16), and light chain CDR3 having the sequence: LQYASYPRT (SEQ ID NO:17).

Determining and quantifying methods may be performed in-vitro or ex-vivo according to some embodiments or may be used in diagnosing conditions associated with expression of TIGIT. The antibodies according to the present invention may be also used to configure screening methods. For example, an enzyme-linked immunosorbent assay (ELISA), or a radioimmuno assay (RIA)can be constructed for measuring levels of secreted or cell-associated polypeptide using the antibodies and methods known in the art.

According to one embodiment a method is provided for detecting or quantifying the presence of TIGIT, comprising the steps of:
  i. incubating a sample with an antibody specific to TIGIT or an antibody fragment thereof comprising at least an antigen-binding portion:
  ii. detecting the bound TIGIT using a detectable probe.

According to some embodiments, the method further comprises the steps of:
  iii. comparing the amount of (ii) to a standard curve obtained from a reference sample containing a known amount of TIGIT; and
  iv. calculating the amount of the TIGIT in the sample from the standard curve.

According to some particular embodiments the sample is a body fluid.

According to some embodiments, the method is performed in-vitro or ex-vivo.

A kit for measuring the expression of TIGIT in biological sample is also provided comprising at least one antibody or antibody fragment comprising the complementarity determining regions (CDRs) selected from the group consisting of: (i) heavy chain CDR1 having the sequence: GYTFTSY-GIS (SEQ ID NO:1), heavy chain CDR2 having the sequence: EIYPRSGNTYYNEKFKG (SEQ ID NO:2), heavy chain CDR3 having the sequence: KGPYYTKNEDY (SEQ ID NO:3), light chain CDR1 having the sequence: RASEHIYYSLA (SEQ ID NO:4), light chain CDR2 having the sequence: NANSLED (SEQ ID NO:5), and light chain CDR3 having the sequence: KQAYDVPRT (SEQ ID NO:6); and (ii) heavy chain CDR1 having the sequence IYCIH (SEQ ID NO: 12), heavy chain CDR2 having the sequence: EISPSNGRTIYNEKFKN (SEQ ID NO:13), heavy chain CDR3 having the sequence: SDGYDGYYFDY (SEQ ID NO:14), light chain CDR1 having the sequence: RASQEIS-GYLN (SEQ ID NO:15), light chain CDR2 having the sequence: AASTLDS (SEQ ID NO:16), and light chain CDR3 having the sequence: LQYASYPRT (SEQ ID NO:17).

In some embodiments, the invention provides a method of diagnosing, assessing the severity or staging an immune-related disease or a proliferative disease comprising determining the expression or activity of TIGIT in a sample from a subject using an antibody according to the present invention or a fragment or conjugate thereof, and comparing the expression or activity of TIGIT to a reference amount of TIGIT expression or activity. Said reference amount may be obtained from a sample taken from a normal subject, from the same subject while being in a different stage of the disease or is determined from clinical data of a large population of subjects.

Antibodies, antibody fragments or conjugates thereof, according to the present invention may be used in any diagnostic, therapeutic or prophylactic method that utilizes binding to the human protein TIGIT, as long as they are capable of specifically binding to said protein and inhibiting it's binding to at least one ligand.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A. FACS histogram plot of $2*10^5$ YTS cells (Left) or YTS cells over-expressing TIGIT (right). Left gray filled curves represent the staining with control mouse IgG (mIgG). Right empty curves represent the staining with two anti human TIGIT mAbs as indicated (VSIG9 #1 and 258-CS1 #4).

FIG. 1B. FACS histogram plots of TIGIT expression on NK cells of two healthy donors (I and II as indicated). Left gray filled curves represent the staining with control mIgG. Right empty curve represents the staining with anti TIGIT (Clone VSIG9 #1).

FIG. 1C. FACS histogram plots of TIGIT expression on CD8+ TILs cells from two melanoma patients (TIL-I and TIL-II). Left gray filled curve represents the staining with control mIgG. Right empty curve represents the staining with anti TIGIT (Clone VSIG9 #1).

FIG. 2A. FACS histogram plot of HepG2 cells (that express high levels of PVR, Nectin-2 and Nectin-3) that were incubated with hTIGIT-Fc (1), hTIGIT-Fc with control mIgG (2) or hTIGIT-Fc with anti-TIGIT mAb VSIG9 #1 at the indicated concentrations (3 and 4).

FIG. 2B. FACS histogram plot of TIGIT ligands (empty histograms) expressed by HepG2 cells indicated at the individual plots. Grey filled histograms represent staining with control mIgG only.

FIG. 3A. Specific killing activity was measured for $^{35}$S labeled 721.221-PVR cells that were incubated with YTS-TIGIT cells (at ratio of 1:10) and with either control mIgG, (left bar) or anti TIGIT-VSIG9 #1 (right bar). *p<0.005.

FIG. 3B. Specific killing activity was measured for $^{35}$S labeled MDA-MB-231 breast cancer cells that were incubated with NK cells from healthy donor (at ratio of 1:10) and with control mIgG (left bar) or anti TIGIT mAb VSIG9 #1 (right bar). **p<0.002.

FIG. 3C. Specific killing activity was measured for $^{35}$S labeled Mel 562 cells that were incubated with NK cells from healthy donor (at ratio of 1:10) and with control mIgG (right bar), anti-TIGIT VSIG9 #1 (left bar), or with anti TIGIT 258-CS1 #4 (central bar). ** p<0.05.

FIG. 3D. Antibody-dependent cell-mediated cytotoxicity (ADCC) activity was measured for $^{35}$S labeled HepG2 cells that were incubated with anti-EGFR mAb (Erbitux®) and added to NK cells pre-incubated with control mAb (left bar) or with anti-VSIG9 #1 (right bar) (at ratio of 10:1, Effectors: Target cells, respectively). **p<0.0007.

FIG. 6A. FACS histogram plots of VSIG9 #1 and the commercial antibody MBSA43 binding to TIGIT. YTS-TIGIT cells (75*103) were stained with anti-TIGIT antibodies VSIG9 #1 (black open histogram) or MBSA43 (grey open histogram) at a concentration range of from 250 nM to 65 fM in serial dilutions. Background—staining of mIgG (grey filled histograms). Each panel represents a specific concentration of the antibodies as indicated. Y-axis of each panel is cell counts and X-axis is fluorescence intensity (FL1-H).

FIG. 6B. Graphical analysis of the binding described in FIG. 6A. Half of the maximal intensity is achieved at the indicated points (MBSA43 grey dashed, mAb VSIG #9 #1 black dashed).

FIG. 7A. Histogram plots of YTS-TIGIT cells staining. 75*103 YTS-TIGIT cells were incubated with 2.5 pmole PVR-Fc (Grey open histograms) in the presence of VSIG9 #1 (Black open histograms) or MBSA43 (grey dashed histograms) at a range of antibody concentrations from 27 to 0.014 pmole in a series of two fold dilutions. The bound PVR was detected by anti Alexa Fluor® 488 Mouse anti human IgG (BioLegend).

FIG. 7B. Histogram plots of YTS-TIGIT cells staining. 75*103 YTS-TIGIT cells were incubated with 2.5 pmole PVR-Fc in the presence of VSIG9 #1 (black open histograms) or MBSA43 (Grey dashed histograms) at a range of concentrations from 27 to 0.014 pmole in a series of two fold dilutions. The bound anti TIGIT was detected by Alexa Fluor® 647 Goat anti-mouse IgG (BioLegend).

Figure 7A:
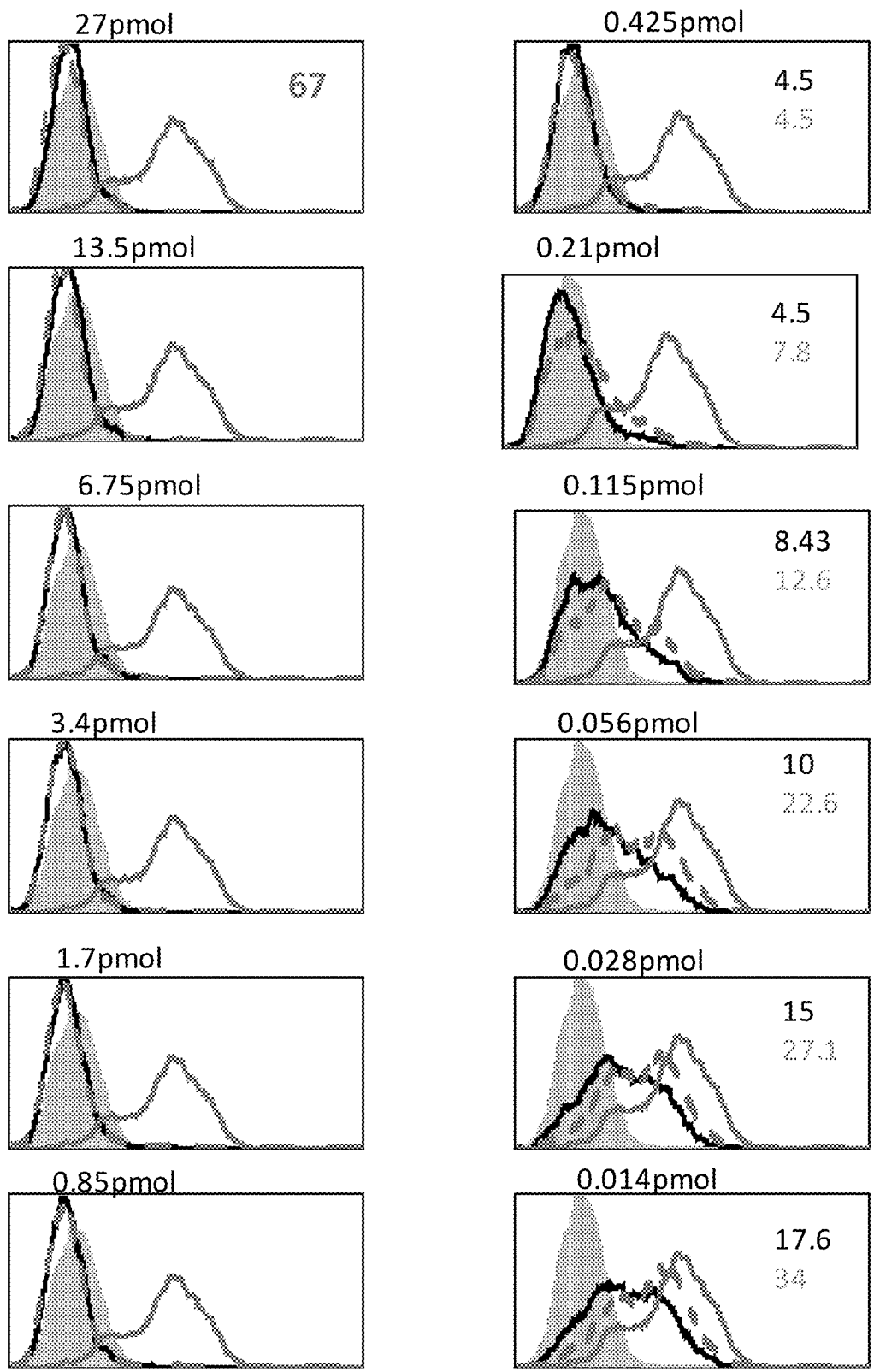
FIGS. 7A and 7B. The VSIG #9 antibody is significantly more potent in preventing PVR-TIGIT interactions than the commercial antibody MBSA43 as measured by FACS analysis.
Figure 7B:
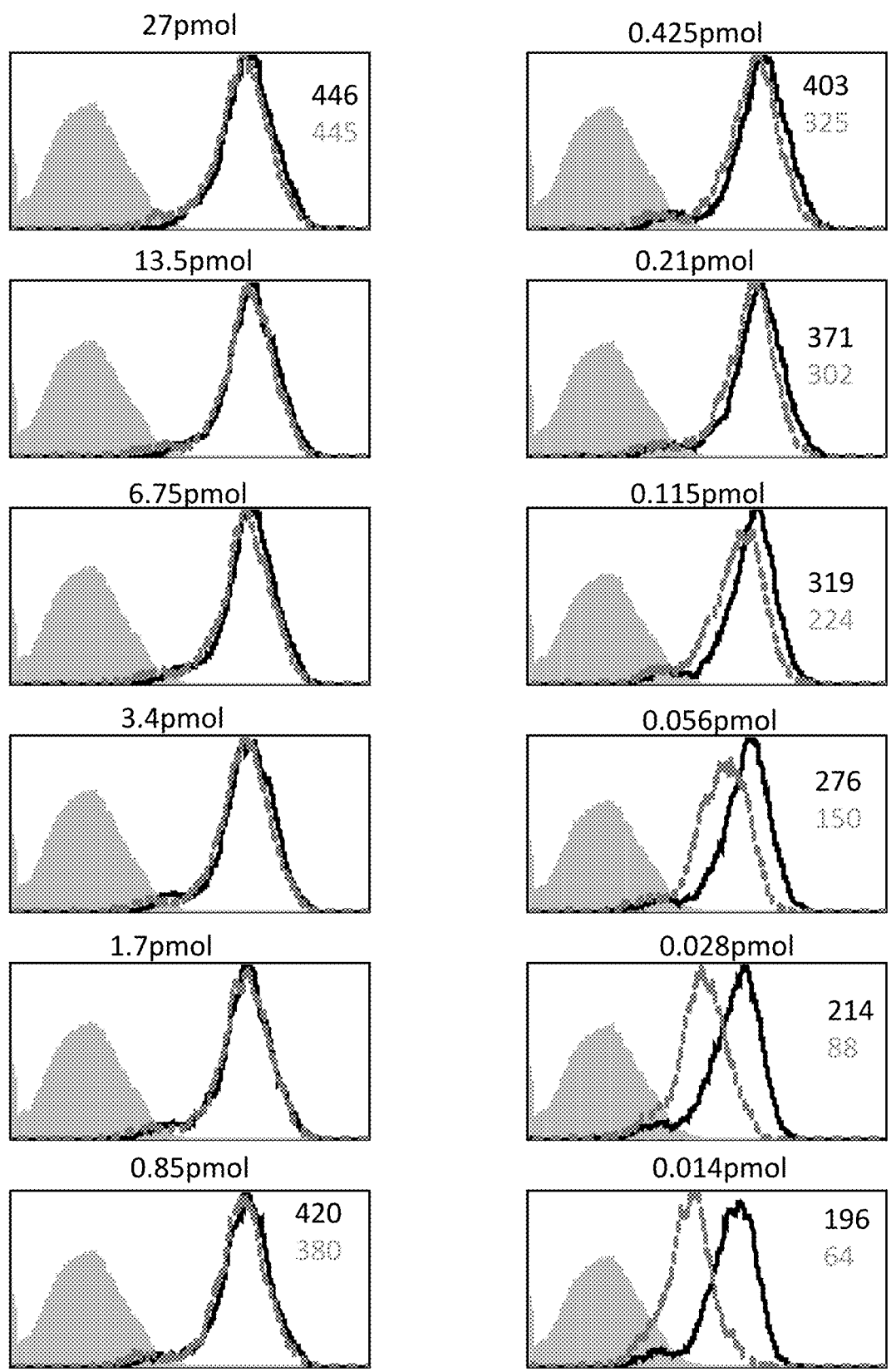

Each panel in FIGS. 7A and 7B represents a specific concentration of the antibodies as indicated. Y-axis of each panel is cell counts and X-axis is fluorescence intensity (FL1-H/FL-4). The numbers in the panel indicates Mean Fluorescent Intensity (MFI).

Figure 8:
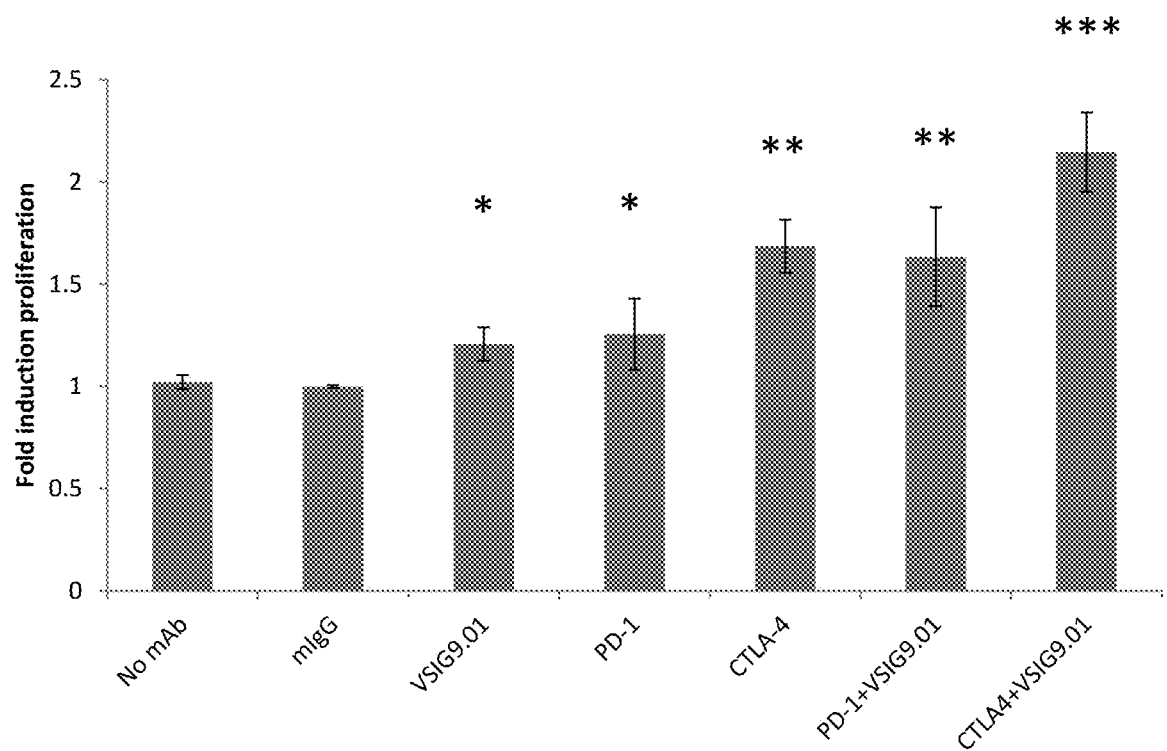

FIG. 8: Blocking of TIGIT by mAb VSIG9 #1 (Vsig9.01) induces T cell proliferation alone or in combination with anti-PD-1 and anti-CTLA4. PBMCs from healthy donors were labeled with 5(6)-Carboxyfluorescein N-hydroxysuccinimidyl ester (CFSE) and activated by anti-CD3 antibodies followed by incubation with MDA-MB-231 cells over expressing hCD80 in presence of 4 μg/ml of the indicated mAbs for 5-9 days. Proliferation was measured by CFSE dilutions. Representative data from at least 5 different experiments is shown. *p<0.04 <0.015 *<0.0004.

Figure 9:
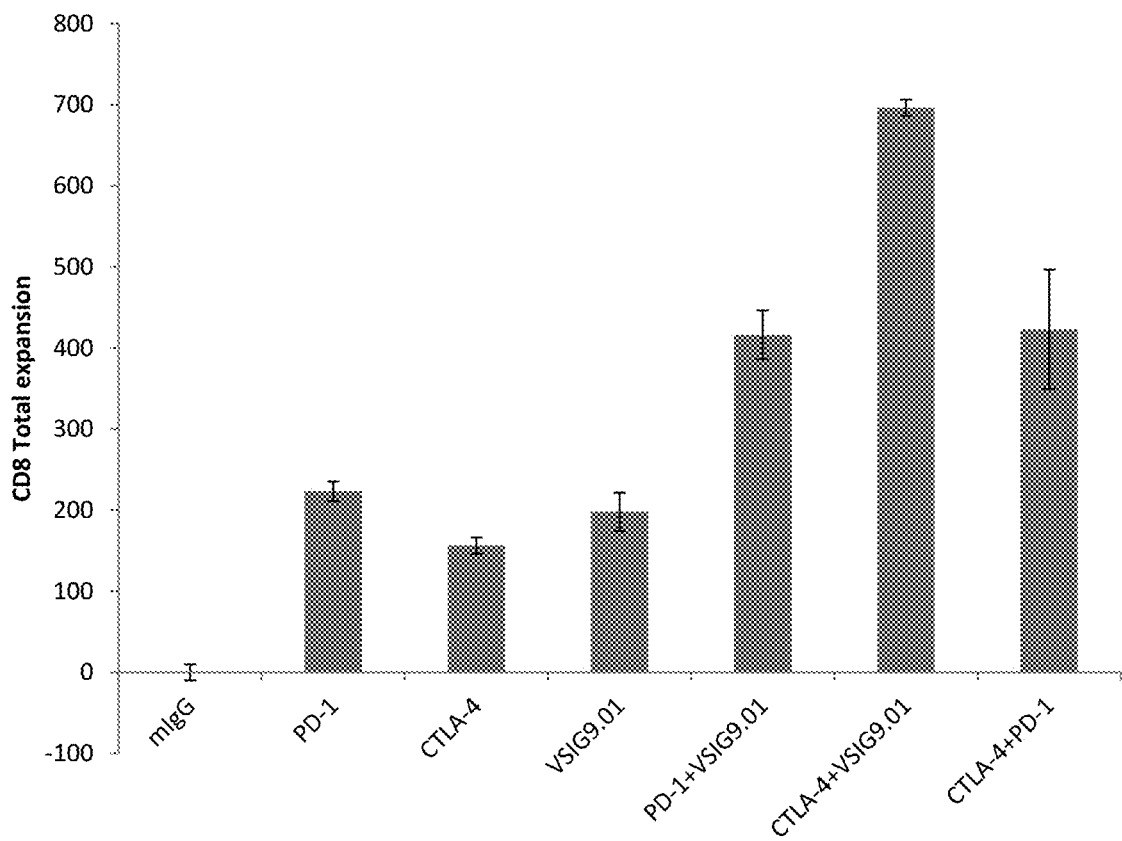

FIG. 9: Anti-TIGIT VSIG9 #1 mAb synergize with anti PD-1 and anti CTLA-4 in increasing CD8 T cells in AML cells. Immune cells separated from bone marrow aspirate obtained from an AML patient were co-cultured with 4 μg/ml of anti TIGIT, anti PD-1 and/or anti CTLA-4 antibodies for 12 day and the amount of CD8 T cells were then determined.

DETAILED DESCRIPTION OF THE INVENTION

The present invention provides monoclonal antibodies specific to the human protein TIGIT, some of the mAbs having exceptional high affinity to this protein and some have dual specificity, and can bind different domains of the protein. The invention also provides production and use of the mAbs as therapeutic agents. In particular, the mAbs of the present invention may be used, alone or in combination with other agents, for restoring and augmenting anti-tumor killing activity of NK and other cells, and as diagnostic reagents.

The term "antigen" as used herein refers to a molecule or a portion of a molecule capable of eliciting antibody formation and being specifically bound by an antibody. An antigen may have one or more than one epitope. The specific binding referred to above is meant to indicate that the antigen will react, in a highly selective manner, with its corresponding antibody and not with the multitude of other antibodies which may be evoked by other antigens. An antigen according to some embodiments of the present invention is a TIGIT protein, having an accession number selected from the group consisting of: NP_776160.2: Q495A1.1; AAI01290.1; AAI01291.1; AAI01292.1; ACD74757.1; EAW79602.1; and AIC53385.1; or a fragment of any of said TIGIT proteins.

According to some embodiments the monoclonal antibodies of the present invention are specific to human TIGIT. According to yet other embodiments, mAb according to the invention bind human TIGIT and at least one TIGIT from other species, such as mouse, monkey, dog or others. According to some specific embodiments, mAbs bind to human TIGIT and to at least one TIGIT monkey species.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1).

The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDRs 1-3). These domains contribute specificity and affinity of the antigen-binding site.

CDR determination—CDR identification from a given heavy or light chain variable sequence, is typically made using one of few methods known in the art. For example, such determination is made according to the Kabat (Wu T. T and Kabat E. A., *J Exp Med*, 1970; 132:211-50) and IMGT (Lefranc M-P, et al., *Dev Comp Immunol*, 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hypervariable regions, namely the unique CDR sequences of both light and heavy chains that together form the antigen-binding site.

The isotype of the heavy chain (gamma, alpha, delta, epsilon or mu) determines immunoglobulin class (IgG, IgA, IgD, IgE or IgM, respectively). The light chain is either of two isotypes (kappa, K or lambda, λ.) found in all antibody classes.

The term "antibody" is used in the broadest sense and includes monoclonal antibodies (including full length or intact monoclonal antibodies), polyclonal antibodies, multivalent antibodies, multi-specific antibodies (e.g., bi-specific antibodies), and antibody fragments long enough to exhibit the desired biological activity, namely binding to human TIGIT.

Antibody or antibodies according to the invention include intact antibodies, such as polyclonal antibodies or monoclonal antibodies (mAbs), as well as proteolytic fragments thereof, such as the Fab or F(ab')$_2$ fragments. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains: (ii) the Fab' fragment, which is a Fab fragment having one or more cysteine residues at the C-terminus of the CH1 domain: (iii) the Fd fragment having VH and CH1 domains: (iv) the Fd' fragment having VH and CH1 domains and one or more cysteine residues at the C-terminus of the CH1 domain: (v) the Fv fragment having the VL and VH domains of a single arm of an antibody: (vi) the dAb fragment (Ward et al., Nature 1989, 341, 544-546) which consists of a VH domain: (vii) isolated CDR regions: (viii) F(ab')$_2$ fragments, a bivalent fragment including two Fab' fragments linked by a disulphide bridge at the hinge region: (ix) single chain antibody molecules (e.g. single chain Fv: scFv) (Bird et al., Science 1988, 242, 423-426; and Huston et al., PNAS (USA) 1988, 85, 5879-5883): (x) "diabodies" with two antigen binding sites, comprising a heavy chain variable domain (VH) connected to a light chain variable domain (VL) in the same polypeptide chain (see, e.g., EP 404,097: WO 93/11161; and Hollinger et al., Proc. Natl. Acad. Sci. USA, 1993, 90, 6444-6448): (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

Single chain antibodies can be single chain composite polypeptides having antigen binding capabilities and comprising amino acid sequences homologous or analogous to the variable regions of an immunoglobulin light and heavy chain i.e. linked VH-VL or single chain Fv (scFv). Techniques for the production of single-chain antibodies (U.S. Pat. No. 4,946,778) can be adapted to produce single-chain antibodies to TIGIT.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). Monoclonal antibodies may also be isolated from phage antibody libraries using the techniques described, for example, in Clackson et al., Nature 1991, 352, 624-628 or Marks et al., J. Mol. Biol., 1991, 222:581-597.

The design and development of recombinant monovalent antigen-binding molecules derived from monoclonal antibodies through rapid identification and cloning of the functional variable heavy (VH) and variable light (VL) genes and the design and cloning of a synthetic DNA sequence optimized for expression in recombinant bacteria are described in Fields et at. 2013, 8(6): 1125-48.

The mAbs of the present invention may be of any immunoglobulin class including IgG, IgM, IgE, IgA. A hybridoma producing a mAb may be cultivated in-vitro or in-vivo. High titers of mAbs can be obtained by in-vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant mAbs one can use various methods all based on display libraries to generate a large pool of antibodies with different antigen recognition sites. Such a library can be made in several ways: One can generate a synthetic repertoire by cloning synthetic CDR regions in a pool of H chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided, for example in Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human CDRs are inserted into a human antibody or consensus antibody FR sequence. Further changes can then be introduced into the antibody framework to modulate affinity or immunogenicity.

For example, U.S. Pat. No. 5,585,089 of Queen et al. discloses a humanized immunoglobulin and methods of preparing same, wherein the humanized immunoglobulin comprises CDRs from a donor immunoglobulin and VH and VL region FRs from human acceptor immunoglobulin H and L chains, wherein said humanized immunoglobulin comprises amino acids from the donor immunoglobulin FR outside the Kabat and Chothia CDRs, and wherein the donor amino acids replace corresponding amino acids in the acceptor immunoglobulin H or L chain frameworks.

Also, transgenic mice, or other organisms such as other mammals, can be used to express humanized antibodies.

U.S. Pat. No. 5,225,539, of Winter, also discloses an altered antibody or antigen-binding fragment thereof and methods of preparing same, wherein a V domain of the antibody or antigen-binding fragment has the FRs of a first immunoglobulin H or L chain V domain and the CDRs of a second immunoglobulin VH or VL domain, wherein said second immunoglobulin VH or VL domain is different from said first immunoglobulin VH or VL domain in antigen binding specificity, antigen binding affinity, stability, species, class or subclass.

Anti-idiotype antibodies specifically immunoreactive with the hypervariable regions of an antibody of the invention are also comprehended.

Alternatively, phage display technology can be utilized to select antibody genes with binding activities towards human TIGIT either from repertoires of PCR amplified v-genes of lymphocytes from humans screened for possessing anti-VEGF or from libraries (McCafferty, et al., (1990), Nature 348, 552-554: Marks, et al., (1992) Biotechnology 10, 779-783). The affinity of these antibodies can also be improved by, for example, chain shuffling (Clackson et al., (1991) Nature 352:628).

The above-described antibodies can be employed to isolate or to identify clones expressing the polypeptides to purify the polypeptides by, for example, affinity chromatography.

The invention provides a monoclonal antibody or an antibody fragment comprising an antigen binding domain (ABD) which comprises three CDRs of a light chain and three CDRs of a heavy chain, wherein said ABD has at least 90% sequence identity or similarity with an ABD of a monoclonal mouse antibody comprising: (i) a heavy variable chain comprising the amino acid sequence SEQ ID NO:7 and a light variable chain comprising the amino acid sequence SEQ ID NO:8 (herein identified as VSIG9 #1); or a heavy variable chain comprising the amino acid sequence SEQ ID NO:18 and a light variable chain comprising the amino acid sequence SEQ ID NO:19 (herein identified as 258-CS1 #4 (or #4)). Such antibody may have an ABD domain having at least 93%, at least 94%, at least 95%, at least 96, at least 97, at least 98, at least 99% sequence identity or similarity or 100% sequence identity with corresponding ABD of VSIG9 #1 or 258-CS1 #4.

Sequence identity is the amount of amino acids or nucleotides which match exactly between two different sequences. Sequence similarity permits conservative substitution of amino acids to be determined as identical amino acids.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

Analogs and variants of the antibody sequences are also within the scope of the present application. These include but are not limited to conservative and non-conservative substitution, insertion and deletion of amino acids within the sequence. Such modification and the resultant antibody analog or variant are within the scope of the present invention as long as they confer, or even improve the binding of the antibody to the human TIGIT.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration into the islets, targeting to specific beta cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, according to one table known in the art, the following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "human antibody" as used herein refers to an antibody which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art.

The terms "molecule having the antigen-binding portion of an antibody" and "antigen-binding-fragments" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see e.g., WO 93/15210, U.S. patent application Ser. No. 08/256,790, WO 96/13583, U.S. patent application Ser. No. 08/817,788, WO 96/37621, U.S. patent application Ser. No. 08/999,554), dimeric bispecific mini-antibodies (see Muller et al., FEBS Lett. 1998 Jul. 31:432 (1-2):45-9) and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The term "non-fully-humanized monoclonal antibody" as used herein refers to a monoclonal antibody, having a heavy chain and/or a light chain variable domains in which the amino-acid sequences flanking and/or immediately adjacent to the CDRs are not fully human, i.e. are not identical to any known homologous or corresponding sequences taken from natural human antibodies.

Humanized and Human Antibodies

A humanized antibody, typically has a human FR grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986): Riechmann et al., Nature, 332:323-327 (1988); Verhoeven et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human V domain has been substituted by the corresponding sequence from a non-human species. In practice, humanized antibodies are typically human antibodies in which some CDR residues and possibly some FR residues are substituted by residues from analogous sites in rodent antibodies.

The choice of human VH and VL domains to be used in making the humanized antibodies is very important for reducing immunogenicity. According to the so-called "best-fit" method, the sequence of the V domain of a rodent antibody is screened against the entire library of known human-domain sequences. The human sequence which is closest to that of the rodent is then accepted as the human FR for the humanized antibody (Sims et al., J. Immunol., 151:2296 (1993): Chothia et al., J. Mol. Biol., 196:901 (1987)). Another method uses a particular FR derived from the consensus sequence of all human antibodies of a particular subgroup of H or L chains. The same FR may be used for several different humanized antibodies (Carter et al., Proc. Natl. Acad. Sci. USA, 89:4285 (1992): Presta et al., J. Immunol., 151:2623 (1993)).

It is further important that antibodies be humanized with retention of high specificity and affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993): Jakobovits et al., Nature, 362:255-258 (1993): Bruggermann et al., Year in Immuno., 7:33 (1993); and Duchosal et al. Nature 355:258 (1992). Human antibodies can also be derived from phage-display libraries (Hoogenboom et al., J. Mol. Biol., 227:381 (1991): Marks et al., J. Mol. Biol., 222:581-597 (1991): Vaughan et al. Nature Biotech 14:309 (1996)).

Pharmacology

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the antibodies and fragments and conjugates thereof of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.) administration is used for delivering antibodies.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

The term "therapeutically effective amount" refers to an amount of a drug effective to treat a disease or disorder in a mammal. In the case of cancer, the therapeutically effective amount of the drug may reduce the number of cancer cells: reduce the tumor size; inhibit (i.e., slow to some extent and preferably stop) cancer cell infiltration into peripheral organs; inhibit (i.e., slow to some extent and preferably stop) tumor metastasis: inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The cancer amendable for treatment by the present invention includes, but is not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition.

The term "Treatment" as used herein refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, gludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine. According to some embodiments, the topoisomerase inhibitor is selected from the group consisting of topotecan and irenotecan. According to some embodiments, the alkylating agent is selected from the group consisting of busulfan, carmustine, lomustine, chlorambucil, cyclophosphamide, cisplatin, carboplatin, ifosamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

According to some particular embodiments, the anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

Monoclonal antibodies according to the present invention may be used as part of combined therapy with at least one anti-cancer agent. According to some embodiments, the additional anti-cancer agent is an immuno-modulator, an activated lymphocyte cell, a kinase inhibitor or a chemotherapeutic agent.

According to some embodiments, the anti-cancer agent is an immuno-modulator, whether agonist or antagonist, such as antibody against a checkpoint molecule.

Checkpoint immunotherapy blockade has proven to be an exciting new venue of cancer treatment. Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy.

The anti-cytotoxic T lymphocyte 4 (CTLA-4) antibody ipilimumab (approved in 2011) was the first immunotherapeutic agent that showed a benefit for the treatment of cancer patients. The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells. An additional anti-PD-1 agent was filed for regulatory approval in 2014 for the treatment of non-small cell lung cancer (NSCLC). Active research is currently exploring many other immune checkpoints, among them: CEACAM1, lymphocyte activation gene 3 (LAG3), CD137, OX40 (also referred to as CD134), and killer cell immunoglobulin-like receptors (KIR).

According to some specific embodiments, the immuno-modulator is selected from the group consisting of: an antibody inhibiting CTLA-4, an anti-human programmed cell death protein 1 (PD-1), PD-L1 and PD-L2 antibody, an activated cytotoxic lymphocyte cell, a lymphocyte activating agent, an antibody against CEACAM, and a RAF/MEK pathway inhibitor. Each possibility represents a separate embodiment of the present invention.

According to some specific embodiments, the additional immuno-modulator is selected from mAb to PD-1, mAb to PD-L1, mAb to PD-L2, mAb to CEACAM1, mAb to CTLA-4, Interleukin 2 (IL-2) or lymphokine-activated killer (LAK) cell.

According to other embodiments the anti-cancer agent is a chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel: alkylating agents: mechlorethamine, chlorambucil, cyclophosphamide, melphalan, ifosfamide: methotrexate: 6-mercaptopurine: 5-fluorouracil, cytarabine, gemcitabin: podophyllotoxins: etoposide, irinotecan, topotecan, dacarbazin: antibiotics: doxorubicin (adriamycin), bleomycin, mitomycin: nitrosoureas: carmustine (BCNU), lomustine, epirubicin, idarubicin, daunorubicin: inorganic ions: cisplatin, carboplatin; interferon, asparaginase: hormones: tamoxifen, leuprolide, flutamide, and megestrol acetate.

According to some embodiments, the chemotherapeutic agent is selected from alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. One or more chemotherapeutic agents can be used.

In some embodiments the pharmaceutical composition according to the present invention is for use in treating cancer or for use in enhancing the immune response.

The term "enhancing immune response" refers to increasing the responsiveness of the immune system and prolonging its memory. The pharmaceutical composition according to the present invention may be used to stimulate immune system upon vaccination. Thus in one embodiment the pharmaceutical composition can be used for improving vaccination.

In certain embodiments, the cancer is selected from lung, thyroid, breast, colon, melanoma, prostate, hepatic, bladder, renal, cervical, pancreatic, leukemia, lymphoma, myeloid, ovarian, uterus, sarcoma, biliary, and endometrial cells cancer. Each possibility represents a separate embodiment of the invention.

According to some embodiments, a pharmaceutical composition, comprising at least one antibody or fragment thereof according to the present invention, and a pharmaceutical composition, comprising an additional immuno-modulator or a kinase inhibitor, are used in treatment of cancer by separate administration.

According to still another aspect the present invention provides a method of treating cancer in a subject in need thereof comprising administering to said subject a therapeutically effective amount of a monoclonal antibody or antibody fragment according to the present invention.

The term "treating" refers to taking steps to obtain beneficial or desired results, including clinical results. Beneficial or desired clinical results include, but are not limited to, alleviation or amelioration of one or more symptoms associated muscular dystrophy, delay or slowing of that impairment, amelioration, palliation or stabilization of that impairment, and other beneficial results.

The term "effective amount" as used herein refers to a sufficient amount of the monoclonal antibody of the antibody fragment that, when administered to a subject will have the intended therapeutic effect. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to effect a beneficial therapeutic response in the subject over time, including but not limited to inhibition of tumor growth, reduction in the rate of tumor growth, prevention of tumor and metastasis growth and enhanced survival.

Toxicity and therapeutic efficacy of the compositions described herein can be determined by standard pharmaceutical procedures in cell cultures or experimental animals, e.g., by determining the IC50 (the concentration which provides 50% inhibition) and the maximal tolerated dose for a subject compound. The data obtained from these cell culture assays and animal studies can be used in formulating a range of dosage for use in human. The dosage may vary depending inter alia upon the dosage form employed, the dosing regimen chosen, the composition of the agents used for the treatment and the route of administration utilized among other relevant factors. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The term "administering" or "administration of" a substance, a compound or an agent to a subject can be carried out using one of a variety of methods known to those skilled in the art. For example, a compound or an agent can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric and humanized antibodies are expected to have circulatory half-lives of up to four and up to 14-21 days, respectively. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion.

The term "about" means that an acceptable error range, e.g., up to 5% or 10%, for the particular value should be assumed.

The following examples are presented in order to more fully illustrate some embodiments of the invention. They should, in no way be construed, however, as limiting the broad scope of the invention.

Examples

Experimental Procedures

NK cell cytotoxicity of various tumors is inhibited due to ligand binding to the TIGIT protein present on all human NK cells and on various T cells. Anti-hTIGIT mAbs were generated and tested for their ability to antagonize killing inhibition imposed by ligand interaction with hTIGIT.

The following cell lines were used: the human EBV transformed 721.221 cells, the human NK tumor cell line YTS ECO, MEL562 melanoma cells, MDA-MB-231 breast cancer cells and HepG2 human hepatocellular cells. The generation of the various YTS ECO transfectants: YTS hTIGIT was described previously (Stanietsky et al., 2009). All cells were grown in RPMI medium supplemented with 10% FCS.

For killing assays, target cells were grown overnight in the presence of $^{35}$S-Methionine added to a methionine-free media (Sigma). Prior to incubation with the effectors cells (NK cells), cells were washed, counted, and 5000 cells/well were plated. 0.5 μg of mAb of blocking antibody was used. For each target, the spontaneous $^{35}$S release was calculated using cells, which were not incubated with effector cells, and maximum [$^{35}$S]-release was calculated by applying 100 μl 0.1 M NaOH to the target cells. The amount of [$^{35}$S]-release was measured after 5 hours of incubation with effectors (at 37° C.) by a β-counter MicroBeta $^2$(PerkinElmer).

$K_D$ Determination Using Biacore

Surface plasmon resonance (SPR) Biosensor Biacore™ T100 (GE Healthcare) was used to determine Koff, Kon and $K_D$ between the antibodies and TIGIT.

Example 1. Production of Monoclonal Antibodies Specific to TIGIT

Monoclonal antibodies against human TIGIT were generated according to one example, by immunizing with TIGIT-Fc fusion protein. The coding sequence of human TIGIT was produced by cloning as a fusion to the Fc fragment of IgG1. The recombinant fusion protein generated was injected to mice and hybridoma supernatants were tested for specific recognition of YTS NK cell line transfectants expressing TIGIT.

Total RNA was extracted from results hybridoma cells following the technical manual of TRIzol® Reagent (Ambion, Cat. No.: 15596-026) and analyzed by agarose gel electrophoresis. Total RNA was reverse transcribed into cDNA using isotype-specific anti-sense primers or universal primers following the technical manual of PrimeScript™ 1st Strand cDNA Synthesis Kit (Takara, Cat. No.: 6110A). The antibody fragments of VH, VL, CH and CL were amplified according to a standard operating procedure of rapid amplification of cDNA ends (RACE). Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

Results

Two exemplary monoclonal antibodies specific to human TIGIT produced were termed #4 (or 258-cs1 #4) and VSIG9 #1 (or Vsig9.01). These mAbs recognizes YTS cells transfected with human TIGIT as demonstrated in FIG. 1A.

The isolated total RNA of the sample was run alongside a DNA marker Marker III (TIAGEN, Cat No.: MD103) on a 1.5% agarose/GelRed™ gel.

Four microliters of PCR products of each of sample were run alongside the DNA Marker III on 1.5% agarose/Gel-Red™ gel. The PCR products were purified and stored at −20° C. until further use.

The VH, VL of different clones were sequenced. The sequences of the variable regions, listed below, are of the antibodies produced by two hybridoma clones termed VSIG9 #1 and 258-cs1.04. The CDR sequences in each amino acid chain are underlined.

```
Antibody VSIG9 #1 Heavy chain: DNA sequence
                                                  (SEQ ID NO: 9)
CAGGTGCAGCTGCAGGAGTCTGGAGCTGAGCTGGCGAGGCCTGGGGCTTCAGT

GAAGCTGTCCTGCAAGGCTTCTGGCTACACCTTCACAAGCTATGGTATAAGCTG

GGTGAAGCAGAGAACTGGACAGGGCCTTGAGTGGATTGGAGAGATTTATCCCA

GAAGTGGTAATACTTACTACAATGAGAAGTTCAAGGGCAAGGCCACACTGACT

GCAGACAAATCCTCCAGCACAGCGTACATGGAGCTCAGCAGCCTGACATCTGA

GGACTCTGCGGTCTATTTCTGTGCAAGAAAGGGACCCTACTATACTAAGAACGA

GGACTACTGGGGCCAAGGCACCATTCTCACAGTCTCCTCA

Antibody VSIG9 #1 Heavy chain: Amino acids sequence
                                                  (SEQ ID NO: 7)
QVQLQESGAELARPGASVKLSCKASGYTFTSYGISWVKQRTGQGLEWIGEIYPRS

GNTYYNEKFKGKATLTADKSSSTAYMELSSLTSEDSAVYFCARKGPYYTKNEDY

WGQGTILTVSS.

Antibody VSIG9 #1 Light chain: DNA sequence
                                                  (SEQ ID NO: 10)
GACATCCAGATGACTCAGTCTCCAGCCTCCCTGGCTGCATCTGTGGGAGAAACT

GTCACCATCACATGTCGAGCAAGTGAGCACATTTACTACAGTTTAGCATGGTAT

CAGCAGAAGCAAGGGAAATCTCCTCAGCTCCTGATCTATAATGCAAACAGCTTG

GAAGATGGTGTCCCATCGAGGTTCAGTGGCAGTGGATCTGGGACACAATATTCT

ATGAAGATCAACAGCATGCAGCCTGAAGATACCGCAACTTATTTCTGTAAACAG

GCTTATGACGTTCCTCGGACCTTCGGTGGAGGCACCAAGCTGGAAATCAAACGG

G CTGATGCTGCACCAACTGTATCC.

Antibody VSIG9 #1 HLight chain: Amino acids sequence
                                                  (SEQ ID NO: 8)
DIQMTQSPASLAASVGETVTITCRASEHIYYSLAWYQQKQGKSPQLLIYNANSLED

GVPSRFSGSGSGTQYSMKINSMQPEDTATYFCKQAYDVPRTFGGGTKLEIKRADA

APTVS

Antibody 258-cs1.04 (also denoted #4)
Antibody 258-cs1.04 Heavy chain: DNA sequence
                                                  (SEQ ID NO: 20)
CAGGTCCAACTGCTGCAGCCTGGGGCTGAACTGGTGAAGCCTGGGGCTTCAGTG

AAGCTGTCCTGCAAGGCTTCTGGCTACACCTTCACCATCTACTGTATACACTGG

GTGAAGCAGAGGCCTGGACAAGGCCTTGAGTGGATTGGAGAGATTAGTCCTAG

CAACGGTCGTACTATCTACAATGAGAAGTTCAAGAACAAGGCCACACTGACTA

TAGACAAATCCTCCACCACAGCCTACATGCAACTCAGCAGCCTGACATCTGAGG

ACTCTGCGGTCTATTGCTGTGCAATATCGGATGGTTACGACGGATACTACTTTG

ACTACTGGGGCCAAGGCACCACTCTCACAGTCTCCTCA.
```

```
Antibody 258-cs1.04_Heavy chain: Amino acids sequence
                                                 (SEQ ID NO: 18)
QVQLLQPGAELVKPGASVKLSCKASGYTFTIYCIHWVKQRPGQGLEWIGEISPSNG

RTIYNEKFKNKATLTIDKSSTTAYMQLSSLTSEDSAVYCCAISDGYDGYYFDYWG

QGTTLTVSS.

Antibody 258-cs1.04_Light chain: DNA sequence
                                                 (SEQ ID NO: 21)
GACATCCAGATGACCCAGTCTCCATCCTCCTTATCTGCCTCTCTGGGAGAAAGA

GTCAGTCTCACTTGTCGGGCAAGTCAGGAAATTAGTGGTTACTTAAACTGGCTT

CAGCAGAAACCAGATGGAACTATTAAACGCCTGATCTACGCCGCATCCACTTTA

GATTCTGGTGTCCCAAAAAGGTTCAGTGGCAGTAGGTCTGGGTCAGATTATTCT

CTCACCATCAGCAGACTTGAGTCTGAAGATTTTGCAGACTATTACTGTCTACAA

TATGCTAGTTATCCTCGGACGTTCGGTGGAGGCACCAAGCTGGAAATCAAA

Antibody 258-cs1.04_Light chain: Amino acids sequence
                                                 (SEQ ID NO: 19)
DIQMTQSPSSLSASLGERVSLTCRASQEISGYLNWLQQKPDGTIKRLIYAASTLDSG

VPKRFSGSRSGSDYSLTISRLESEDFADYYCLQYASYPRTFGGGTKLEIK.
```

Figure 1A:
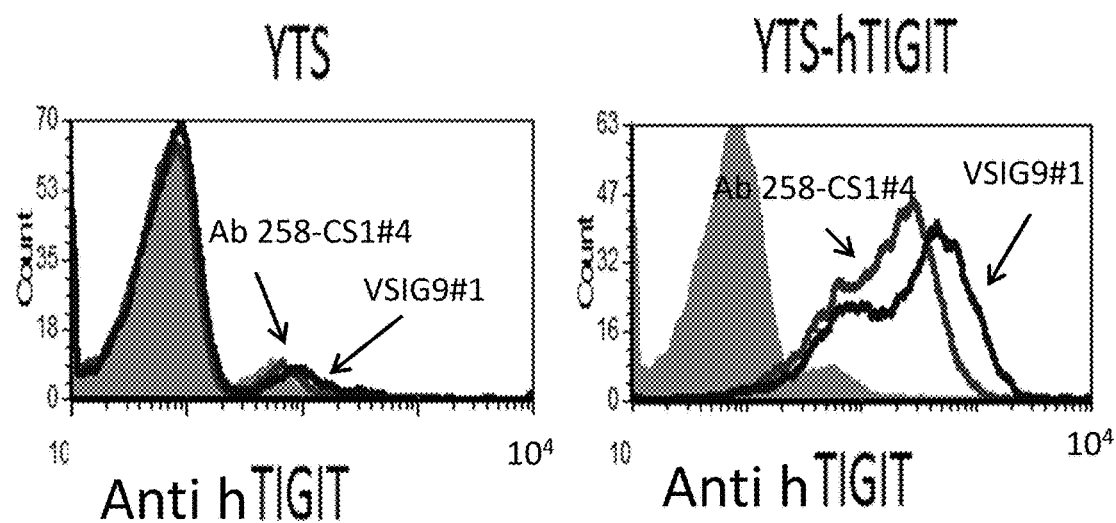
FIGS. 1A-1C. Expression of TIGIT on effector immune cells.
Figure 1B:
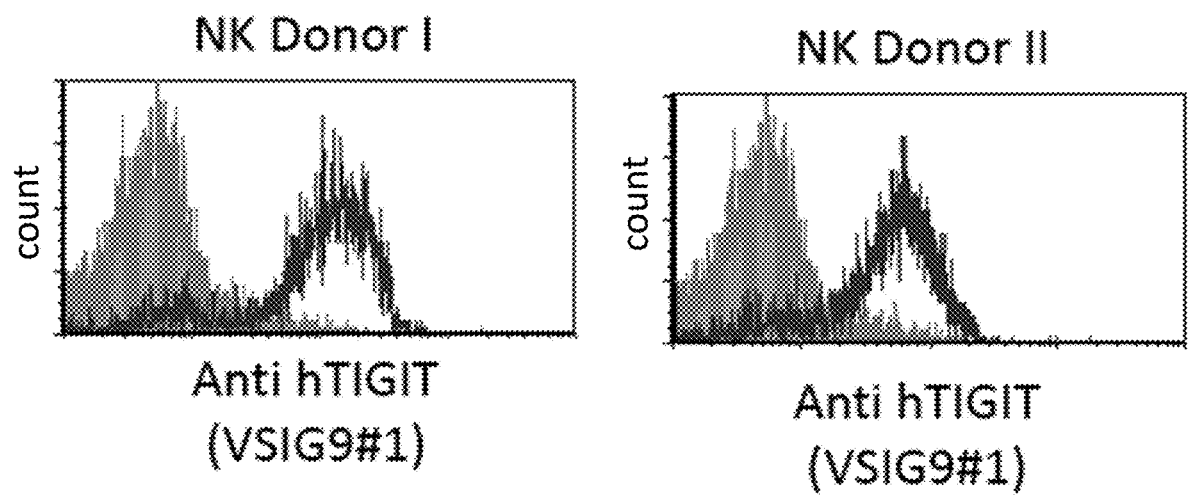
Figure 1C:
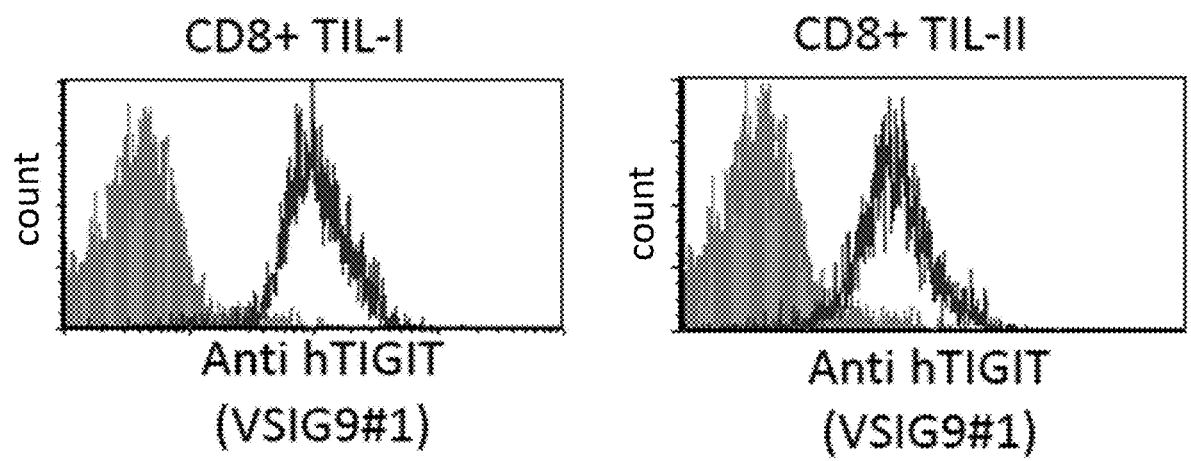

Table 1 lists the CDR and variable region amino acid sequences of the two anti human TIGIT mAb and the variable region sequences.

used as control (left curve). Overall, FIGS. 1A-1C shows broad expression of TIGIT on immune cells and demonstrate that the VSIG9 #1 mAb can bind to immune cells.

TABLE 1

| CDR | VSIG9#1 | SEQ ID No. | 258-cs1.04 | SEQ ID No. |
|---|---|---|---|---|
| HCDR1 | GYTFTSYGIS | 1 | IYCIH | 12 |
| HCDR2 | EIYPRSGNTYYNEKFKG | 2 | EISPSNGRTIYNEKFKN | 13 |
| HCDR3 | KGPYYTKNEDY | 3 | SDGYDGYYFDY | 14 |
| LCDR1 | RASEHIYYSLA | 4 | RASQEISGYLN | 15 |
| LCDR2 | NANSLED | 5 | AASTLDS | 16 |
| LCDR3 | KQAYDVPRT | 6 | LQYASYPRT | 17 |
| VH | Amino acid sequence | 7 | Amino acid sequence | 18 |
| VH | Polynucleotide sequence | 9 | Polynucleotide sequence | 20 |
| VL | Amino acid sequence | 8 | Amino acid sequence | 19 |
| VL | Polynucleotide sequence | 10 | Polynucleotide sequence | 21 |

Example 2. Broad Expression of TIGIT on Effector Immune Cells

To examine the recognition of TIGIT by the mAbs, $2*10^5$ YTS-TIGIT over expressing cells (as previously described by Stanietsky et al., ibid) were incubated with 0.2 microgram of anti TIGIT mAb clone VSIG9 #1 or #4 on ice for 30 min. After two rounds of wash in FACS buffer, goat-anti mouse IgG (H+L) Secondary Antibody Alexa Fluor® 647 conjugate (BioLegend) was added for additional 30 min on ice. As shown in FIG. 1A, the mAbs recognize TIGIT proteins on YTS-TIGIT over expressing cells (right curve), but not on YTS cells. mIgG was used as a control. Next, the VSIG9 #1 was examined on activated NK cells from two healthy donors. As shown in FIG. 1B, the mAb recognized the NK cells (right curve in the FACS histogram plots). mIgG was used as a control (left curve).

Next, the VSIG9 #1 was examined on two CD8+ T cell populations, obtained from melanoma patients (TIL-I and TIL-II). As shown in FIG. 1C, the mAb recognized the T-cells (right curve in the FACS histogram plots). mIgG was

Example 3. Anti-TIGIT VSIG9 #1 Blocks TIGIT-Fc Binding to Tumor Cells

Figure 2A:
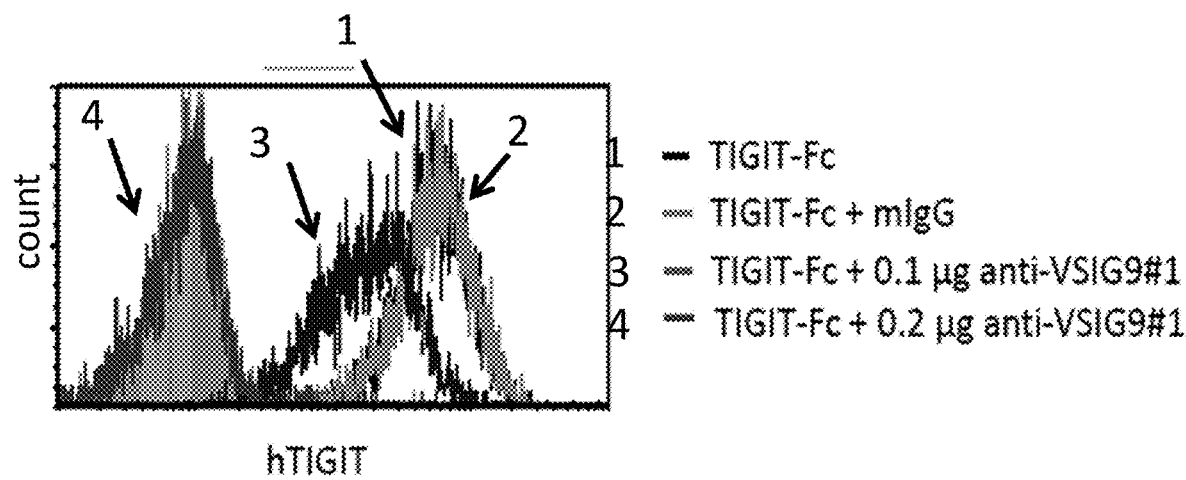
FIGS. 2A-2B. Inhibition of TIGIT binding by mAb VSIG9 #1.
Figure 2B:
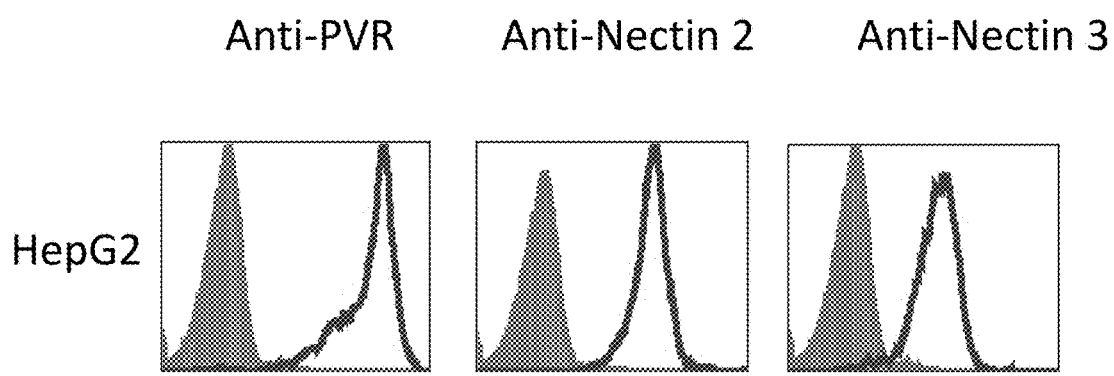

To examine the effect of VSIG9 #1 on TIGIT-Fc binding to tumor cells, $2.5*10^5$ HepG2 cells (that express high levels of PVR, Nectin-2 and Nectin-3) were incubated with 25 microgram/well hTIGIT-Fc with no mAb (FIG. 2A, arrow 1) with mIgG (FIG. 2A, arrow 2) or with anti-TIGIT-VSIG9 #1 at the indicated concentrations (FIG. 2A, arrows 3 and 4) for 30 min on ice, the detection was done using Alexa Fluor® 647 anti-human IgG (BioLegend). The expression of TIGIT ligands, PVR, Nectin-2 and Nectin-3 on the HepG2 cells is demonstrated in FIG. 2B.

The results demonstrate that the mAb can prevent TIGIT binding to tumor cells, suggesting that the antibody is capable of preventing the inhibition of the immune response.

Example 4. VSIG9 #1 mAb Enhances Killing Activity

Figure 3A:
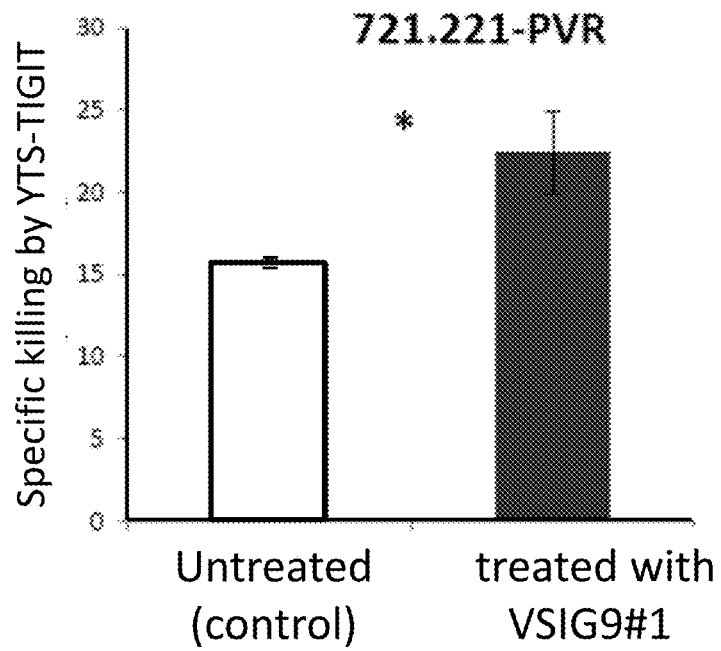
FIGS. 3A-3D. Blocking of TIGIT leads to enhanced killing activity.
Figure 3B:
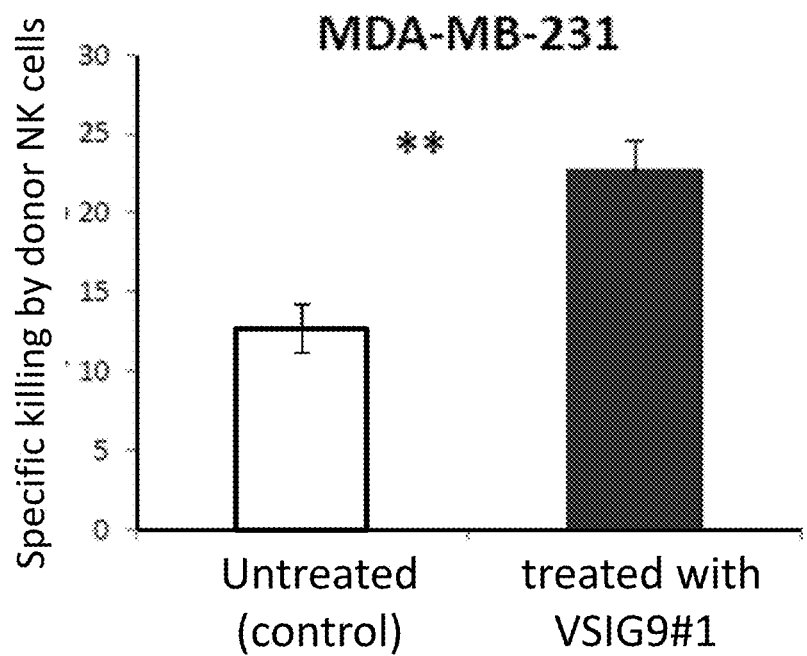
Figure 3C:
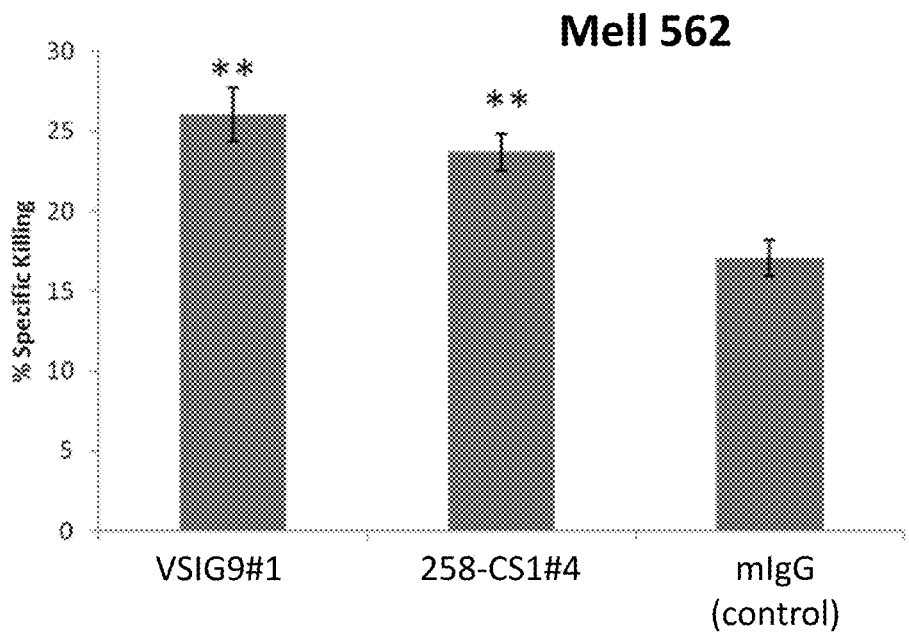
Figure 3D:
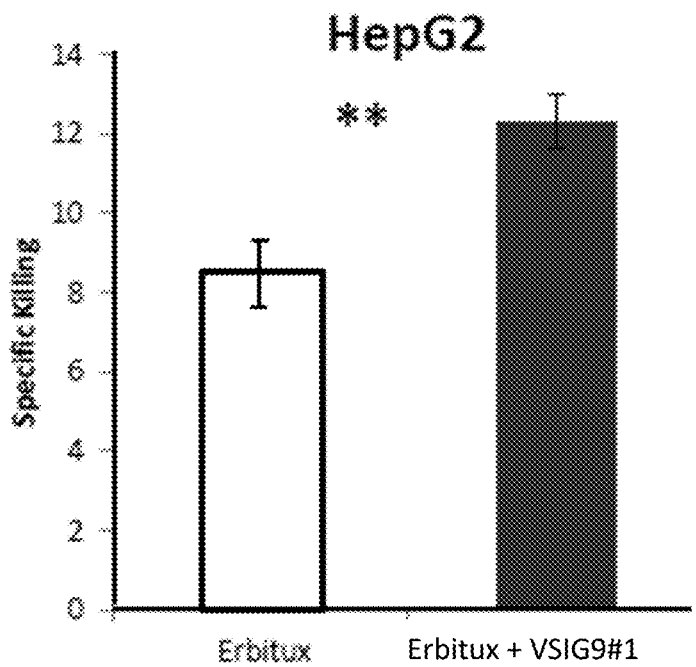

To examine the effect of anti-TIGIT mAbs on the killing activity of effector cells, YTS-TIGIT NK cells were incubated with $^{35}S$ labeled 721.221-PVR cells in the presence of 2.5 microgram/ml of control mIgG (left bar) or anti-TIGIT VSIG9 #1 (right bar)(*p<0.02). The specific killing was calculated as previously described (Stanietsky et. al ibid). The killing percentage was examined after 5 hours. As shown in FIG. 3A, anti TIGIT mAb VSIG9 #1 enhances killing activity. Next, the specific killing activity was examined for MDA-MB-231 human breast tumor cells that were labeled with $^{35}$S and incubated with NK cells from healthy donors in the presence of control mIgG (left bar) or VSIG9 #1 (right bars). Killing percentage was measured after 5 hours (p<0.002). As shown in FIG. 3B, VSIG9 #1 enhances the killing effect. The specific killing activity of two antibodies was also examined with MEL562 melanoma cells. As shown in FIG. 3C, the two mAbs, 258-CS1 #4 (central bar) and VSIG9 #1 (left bar) significantly enhances (p<0.05) the killing effect of these cells compared to control antibody mIgG (right bar). Finally, antibody-dependent cell-mediated cytotoxicity (ADCC) of VSIG9 #1 was examined on human hepatocellular HepG2 cells labeled with $^{35}$S that were incubated with anti-EGFR mAb (Erbitux R) and added to NK cells that were pre-incubated with control mAb (left bar) or with VSIG9 #1 (right bar) at a ratio of 10:1 Effector cells: Target cells, respectively. (***p<0.0007). A shown in FIG. 3D, VSIG9 #1 is capable of enhancing the killing effect.

The results demonstrate that the tested anti human mAbs VSIG9 #1 and 258-CS1 #4 are capable of enhancing the killing effect on different target cells and in a variety of conditions. The mAbs prevent the inhibitory effect of the TIGIT receptor and are therefore suitable for use as anti-cancer agents.

Example 5. Antibodies #4 and VSIG9 #1 Block TIGIT Binding to PVR

Figure 4A:
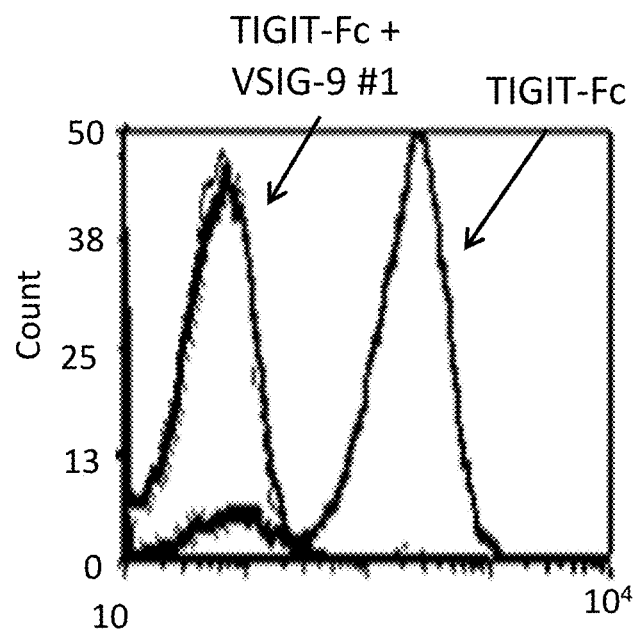
FIGS. 4A-4B. Antibodies 258-CS1 #4 and VSIG9 #1 block TIGIT binding to PVR. HepG2 cells that express the TIGIT ligand PVR were incubated with TIGIT-Fc or TIGIT-Fc following pre-incubation with mAb VSIG9 #1 (FIG. 4A), or with mAb 258-CS1 #4 (FIG. 4B) and binding was measured using FACS.
Figure 4B:
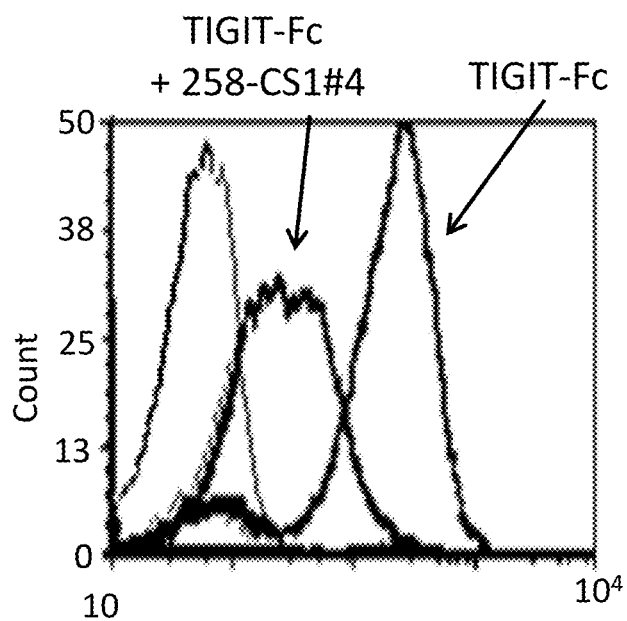

To examine the ability of mAbs 258-CS1 #4 and VSIG9 #1 to block the interaction of TIGIT which its ligands, HepG2 cells that express PVR, Nectin-2 and Nectin-3 were incubated with TIGIT-Fc or TIGIT-Fc following pre-incubation with mAb VSIG-9 #1 (FIG. 4A), or with mAb 258-CS1 #4 (FIG. 4B). The results showed that pre-incubation of TIGIT-Fc with VSIG-9 #1 completely blocked TIGIT-Fc binding (FIG. 4A), while pre-incubation with mAB 258-CS1 #4 partially blocked TIGIT-Fc binding (FIG. 4B).

Figure 5A:
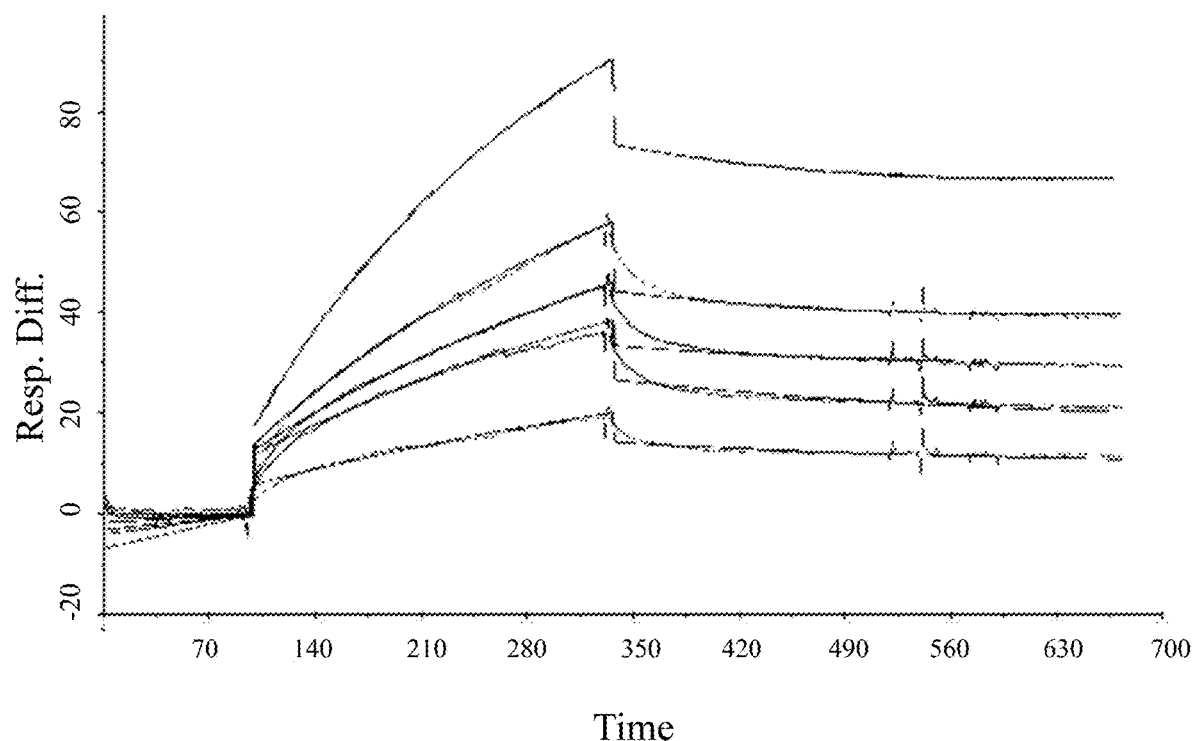
FIGS. 5A-5B. Binding kinetic analyses of the mAbs 258-cs1 #4 (#4) (FIG. 5A) and VSIG9 #1 (FIG. 5B) to biosensor loaded with human TIGIT from two commercial sources, using Biacore.
Figure 5B:
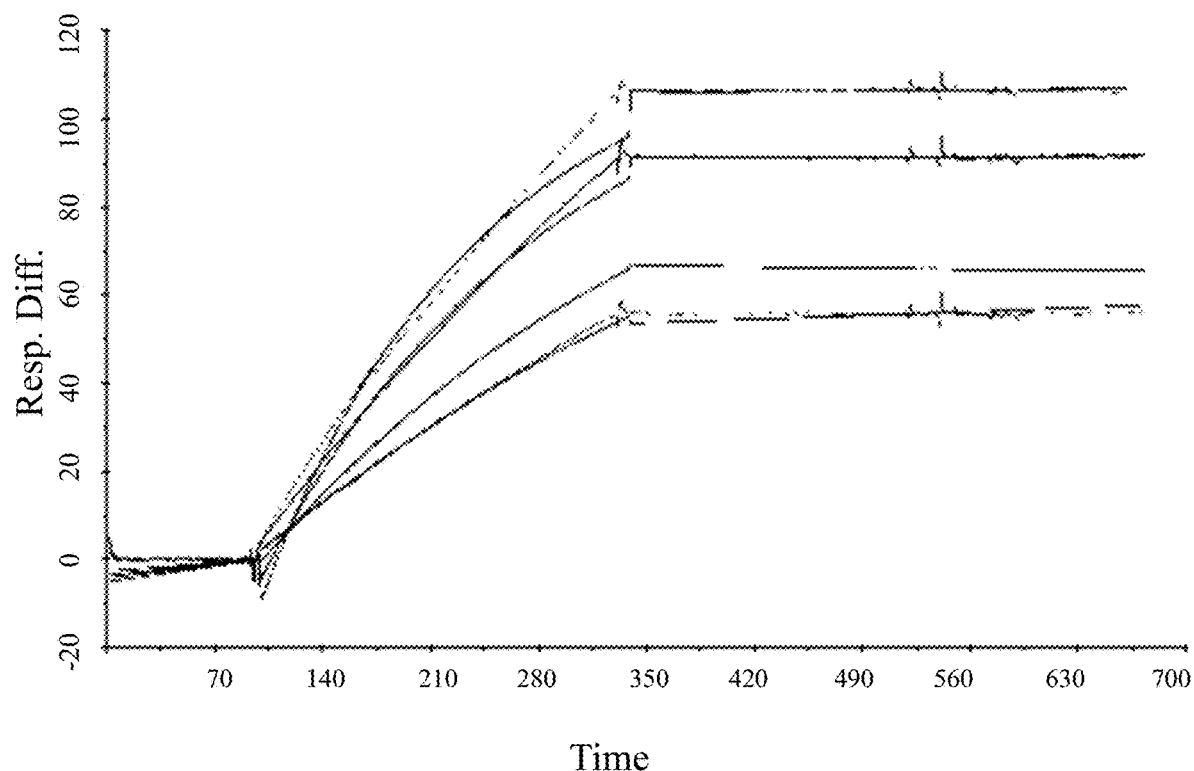

Example 6. Antibodies 258-CS1 #4 and VSIG-9 #1 Exhibit High and Exceptional Affinity to TIGIT Full binding kinetic analyses of the mAbs to human TIGIT from two sources were carried out using Biacore. The results shown in FIGS. 5A and 5B indicate that the two mAbs exhibit high affinity to human TIGIT. While the mAb termed 258-CS1 #4 (#4) had an average Kd of about $1\times10^{-7}$ M (average of $9.96\times10^{-8}$ M and $1.07\times10^{-7}$ M), mAb VSIG-9 #1 binds human TIGIT with an extremely high affinity, having a Kd of $4.5\times10^{-10}$ M (average of $5.13^{-10}$ M and $3.87^{-10}$ M).

It was further demonstrated that mAb VSIG-9 #1 is specific to human TIGIT and does not bind mouse TIGIT.

Example 7. Antibody VSIG9 #1 Exhibits Higher Affinity to TIGIT as Compared to the Commercial Antibody MBSA43

Figure 6A:
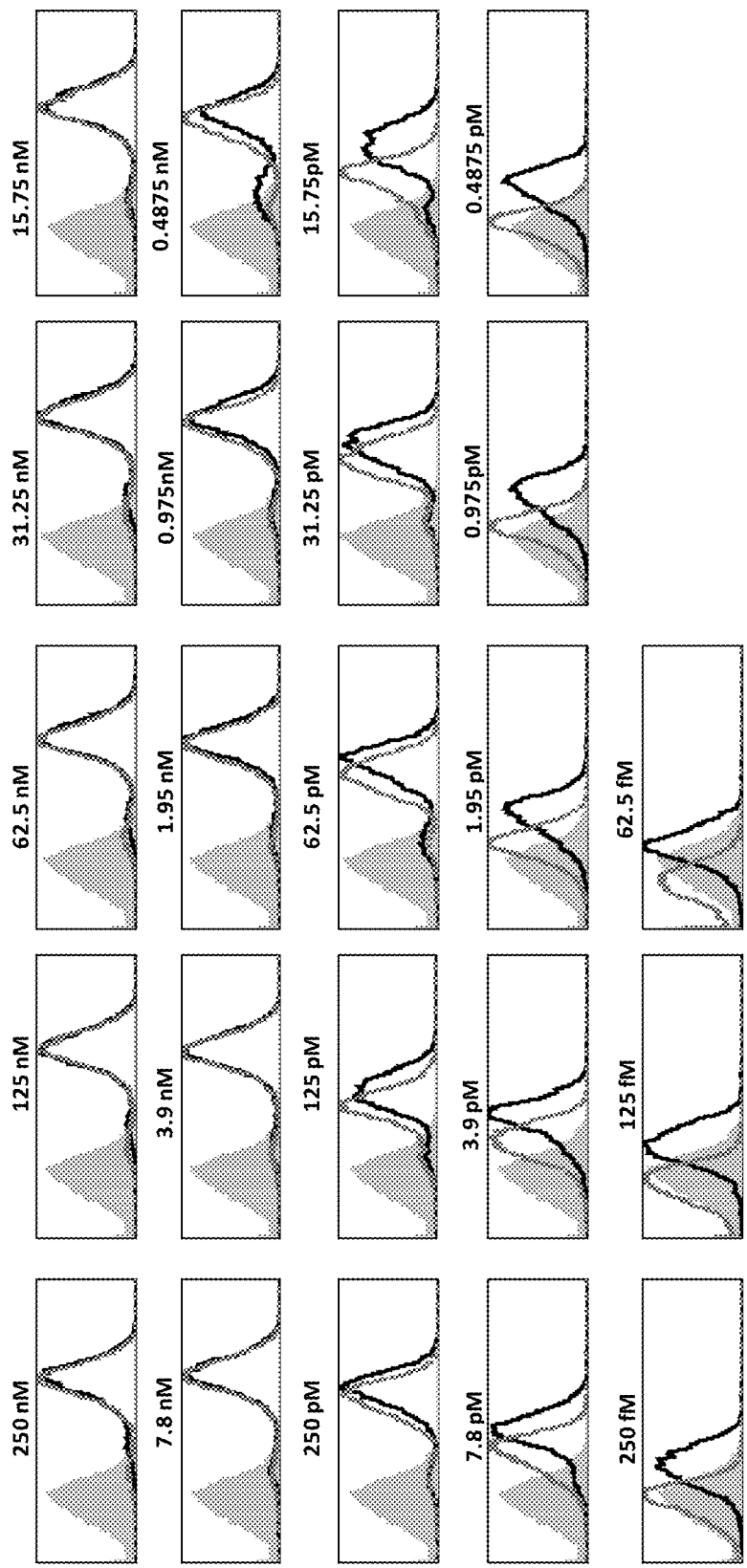
FIGS. 6A-6B. Antibody VSIG9 #1 binds to TIGIT cells significantly stronger than commercial antibody MBSA43 (eBioscience Cat #12-9500-42).
Figure 6B:
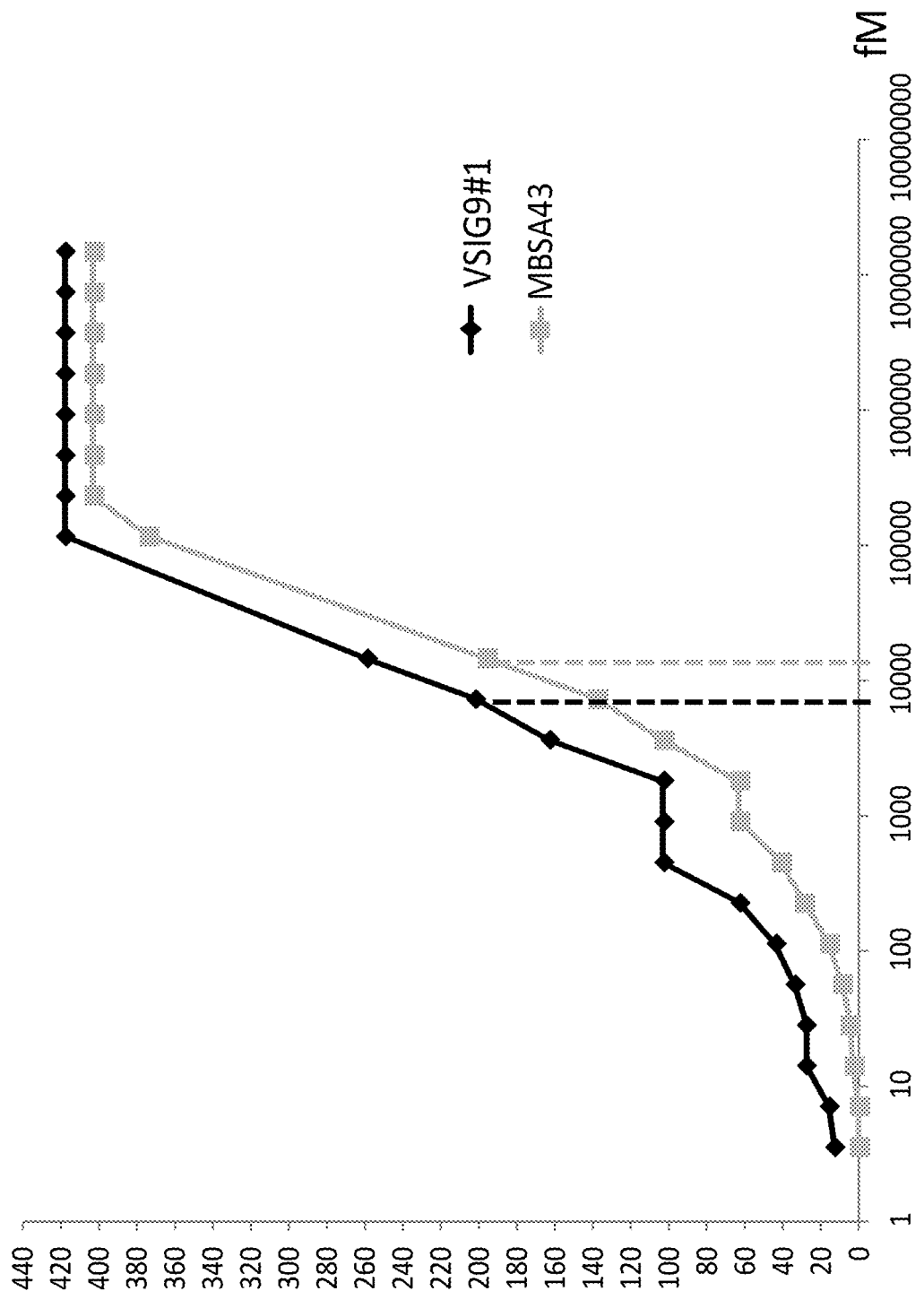

The binding affinity of antibodies VSIG9 #1 and MBSA43 to TIGIT was compared. 75×103 TIGIT expressing YTS cells were stained with the two antibodies at serial dilution concentrations of 250 nM to 65 fM, following determination by FACS. As shown in FIGS. 6A and 6B, VSIG #9 stained the cells at a concentration lower as 62.5 fM, while MBSA43 stained the cells only above 1950 fM (1.95 pM) and did not show staining at the last 4 dilutions Clear staining differences between the two antibodies are seen up to a concentration of 250 pM. The superiority of the VSIG9 #1 antibody compared to the MBSA43 antibody is also depicted in FIG. 6B.

Example 8. The Blocking Activity of VSIG9 #1 is Higher than the One of the Commercial Antibody MBSA43

To examine the anti-TIGIT antibodies blocking effect on PVR-TIGIT binding, a staining assay of TIGIT-expressing YTS cells with PVR-Fc was performed. 75×103 YTS-TIGIT cells were incubated with 2.5 pmole PVR-Fc in the presence of VSIG9 #1 or MBSA43 at a concentration range of from 27 to 0.014 pmole in a series of two fold dilutions.

As shown in FIGs. 7A (detection of bound PVR) and 7B (detection of bound anti TIGIT mAb), the PVR-TIGIT blocking activity of VSIG9 #1 was significantly higher as compared to MBSA43.

The results of Examples 7 and 8 demonstrate that VSIG9 #1 has significant higher affinity to human TIGIT, as compared to MBSA43 and that it is significantly better at preventing the binding of the high affinity ligand (PVR) across a range of concentrations.

Example 9. Anti TIGIT mAb Synergistic Activity with Other Checkpoint Molecule Inhibitors The efficacy of mAb VSIG9 #1 (Vsig9.01), alone or in combination with other immunemodulators, on induction of T cell proliferation by blocking of TIGIT, was examined. PBMCs from healthy donors were labeled with 5(6)-Carboxyfluorescein N-hydroxysuccinimidyl ester (CFSE) and activated with anti-CD3 antibodies followed by incubation for 5-9 days with MDA-MB-231 cells over-expressing hCD80 in the presence of 4 μg/ml of the mAb VSIG9 #1, anti-PD-1 (Keytruda) and anti-CTLA4 (pilimumab), alone or in combination. Proliferation was measured by CFSE dilutions.

The results shown in FIG. 8, collected from at least 5 different experiments, indicate a synergism between the anti TIGIT mAb and anti PD-1 or anti CTLA4, demonstrated by significant increased T-cell proliferation for the combination of VSIG9 #1 with the other checkpoint antibodies (*p<0.04 <0.015 *<0.0004).

Example 10. In Vivo Effect of the Humanized Anti-TIGIT Antibodies in a Mouse Model of Human Tumor The anti-tumor efficacy of the antibodies is studied in vivo. To estimate the efficacy of the antibodies described herein in inhibition of human cancer, the antibody is studied in a model combining both tumors and lymphocytes of human origin. Severe combined immune-deficient mice (SCID) is engrafted with hPBL to restore immune-competence. Mice are challenged with human cancer cells and treated with increasing concentrations of the anti human TIGIT antibody, administered in single- or multi-intravascular dose several days post tumor challenge.

A similar model with tumor lines in SCID mice is performed according to Paine-Murrieta G D, Cancer Chemother Pharmacol. 1997:40(3): 209-14.

Example 11. Inhibition of Human Melanoma (SK-28) in SCID Mice by the Humanized Anti-TIGIT Antibodies To estimate the efficacy of anti-TIGIT antibodies in inhibition of human cancer, the modified antibody is studied in a model combining both tumors and lymphocytes of human origin. Severe combined immune-deficient mice (SCID) is engrafted with hPBL to restore immune-competence. Mice are challenged with human melanoma cells (SK-28) and treated with increasing concentrations of the antibody, administered in a single i.v. dose on day 11 post tumor inoculation.

Similarly, a model described by Hardy el al., Proc Natl Acad Sci USA. 1997 May 27; 94(11): 5756-5760 is employed.

Example 12. Immunotherapy of Human Colorectal Cancer Hepatic Metastases by the Anti-TIGIT mAbs in Nude Mice LIM6 and HM7 are two sub-clones of the human CRC cell line LS174T that were selected for their high mucin synthesis and metastatic potential. The tumor cells are injected into the exposed spleen of anesthetized nude mice. After several minutes, the spleens are removed and the excisions closed. Low doses of anti-TIGIT antibodies of the invention are administered 10 days later and mice are sacrificed 35 days post tumor inoculation. The livers are weighed, the number of metastatic nodules counted, and liver tissue is processed for histology and Immunohistochemistry study.

Additional metastasis models that can be used to test the antibodies and fragments of the present invention were described by Yung at al., Ocul Oncol Pathol. 2015 April: 1(3); 151-160.

Example 13. Anti TIGIT Antibodies have Synergistic Effect on AML Cells

Bone marrow aspirate was obtained from an AML patient, following Ficoll separation the immune cells and the blasts were co-cultured with various antibodies (at 4 µg/ml) for 12 days after 12 days the amount of T cells was established.

As demonstrated in FIG. 9, significant increase in the amount of CD8 T cells was observed in presence of anti-TIGIT VSIG9 #1 mAb. Interestingly blocking of TIGIT had synergistic effect with blocking of PD-1 and CTLA-4.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

---

The invention claimed is:

1. A polynucleotide comprising a sequence encoding the heavy and light chain variable regions of a monoclonal antibody or a fragment thereof, or a first polynucleotide and a second polynucleotide that comprise sequences encoding the heavy chain variable region and the light chain variable region, respectively, of the monoclonal antibody or fragment thereof, wherein the monoclonal antibody or fragment thereof is capable of binding to human T-cell immunoglobulin and ITIM domain (TIGIT), wherein the antibody fragment comprises at least the antigen binding portion of the monoclonal antibody, and wherein the antibody or fragment thereof is selected from the group consisting of:
  (i) an antibody or fragment thereof comprising six complementarity determining regions (CDRs), wherein the heavy chain (HC) CDR1 comprises the sequence GYTFTSYGIS (SEQ ID NO:1) or TSYGIS (SEQ ID NO:11); the HC CDR2 comprises the sequence: EIYPRSGNTYYNEKFKG (SEQ ID NO:2); the HC CDR3 comprises the sequence: KGPYYTKNEDY (SEQ ID NO:3); the light chain (LC) CDR1 comprises the sequence: RASEHIYYSLA (SEQ ID NO:4); the LC CDR2 comprises the sequence: NANSLED (SEQ ID NO:5); and the LC CDR3 comprises the sequence: KQAYDVPRT (SEQ ID NO: 6); and
  (ii) an antibody or fragment thereof comprising six CDRs, wherein the HC CDR1 comprises the sequence IYCIH (SEQ ID NO:12); the HC CDR2 comprises the sequence: EISPSNGRTIYNEKFKN (SEQ ID NO:13); the HC CDR3 comprises the sequence: SDGYDGYYFDY (SEQ ID NO:14); LC CDR1 comprises the sequence: RASQEISGYLN (SEQ ID NO:15); the LC CDR2 comprises the sequence: AASTLDS (SEQ ID NO:16); and the LC CDR3 comprises the sequence: LQYASYPRT (SEQ ID NO:17).

2. The polynucleotide or the first and the second polynucleotides of claim 1, wherein the polynucleotide or the first polynucleotide comprises the sequence set forth in SEQ ID NO:9, or a variant thereof having at least 90% identity to SEQ ID NO:9, encoding the heavy chain variable region of the monoclonal antibody or fragment thereof.

3. The polynucleotide or the first and the second polynucleotides of claim 1, wherein the polynucleotide or the second polynucleotide comprises the sequence set forth in SEQ ID NO: 10, or a variant thereof having at least 90% identity to SEQ ID NO:10, encoding the light chain variable region of the monoclonal antibody or fragment thereof.

4. The polynucleotide or the first and the second polynucleotides of claim 1, wherein the polynucleotide or the first polynucleotide comprises the sequence set forth in SEQ ID NO:20, or a variant thereof having at least 90% identity to SEQ ID NO:20, encoding the heavy chain variable region of the monoclonal antibody or fragment thereof.

5. The polynucleotide or the first and the second polynucleotides of claim 1, wherein the polynucleotide or the second polynucleotide comprises the sequence set forth in SEQ ID NO:21, or a variant thereof having at least 90% identity to SEQ ID NO:21, encoding the light chain variable region of the monoclonal antibody or fragment thereof.

6. The polynucleotide or the first and the second polynucleotides of claim 1, wherein the polynucleotide or the first polynucleotide comprises a sequence encoding the amino acid sequence of the heavy chain variable region of the monoclonal antibody or fragment thereof as set forth in SEQ ID NO: 7.

7. The polynucleotide or the first and the second polynucleotides of claim 1, wherein the polynucleotide or the second polynucleotide comprises a sequence encoding the amino acid sequence of the light chain variable region of the monoclonal antibody or fragment thereof as set forth in SEQ ID NO:8.

8. The polynucleotide or the first and the second polynucleotides of claim 1, wherein the polynucleotide or the first polynucleotide comprises a sequence encoding the amino acid sequence of the heavy chain variable region of the monoclonal antibody or fragment thereof as set forth in SEQ ID NO: 18.

9. The polynucleotide or the first and the second polynucleotides of claim 1, wherein the polynucleotide or the second polynucleotide comprises a sequence encoding the amino acid sequence of the light chain variable region of the monoclonal antibody or fragment thereof as set forth in SEQ ID NO:19.

10. The polynucleotide or the first and the second polynucleotides of claim 1, wherein the monoclonal antibody or fragment thereof is selected from the group consisting of: a bispecific antibody, a humanized antibody, and an antibody conjugate.

11. The polynucleotide or the first and the second polynucleotides of claim 10, wherein the monoclonal antibody or fragment thereof is a bispecific antibody comprising two sets of CDR sequences, wherein:
  one CDR set comprises an HC CDR1 having the sequence GYTFTSYGIS (SEQ ID NO:1) or TSYGIS (SEQ ID NO: 11); an HC CDR2 having the sequence: EIYPRSGNTYYNEKFKG (SEQ ID NO:2); an HC CDR3 having the sequence: KGPYYTKNEDY (SEQ ID NO:3); an LC CDR1 having the sequence: RASEHIYYSLA (SEQ ID NO:4); an LC CDR2 having the sequence: NANSLED (SEQ ID NO:5); and an LC CDR3 having the sequence: KQAYDVPRT (SEQ ID NO:6); and
  a second set comprises an HC CDR1 having the sequence: IYCIH (SEQ ID NO:12), an HC CDR2 having the sequence: EISPSNGRTIYNEKFKN (SEC ID NO:13), an HC CDR3 having the sequence: SDGYDGYYFDY (SEC ID NO:14), an LC CDR1 having the sequence: RASQEISGYLN (SEC ID NO: 15), an LCCDR2 having the sequence: AASTLDS (SEQ ID NO: 16), and an LC CDR3 having the sequence: LQYASYPRT (SEC ID NO:17).

12. A cell comprising the polynucleotide or the first and the second polynucleotides according to claim 1.

13. The cell of claim 12, wherein the cell is a hybridoma cell.

14. A plasmid comprising the polynucleotide or the first and the second polynucleotides according to claim 1.

15. The plasmid of claim 14, comprising a polynucleotide sequence set forth in SEQ ID NO:9, SEQ ID NO:20, or both.

16. The plasmid of claim 14, comprising a polynucleotide sequence set forth in SEQ ID NO: 10, SEQ ID NO:21, or both.

* * * * *

SEQUENCE LISTING

```
<160> NUMBER OF SEQ ID NOS: 21

<210> SEQ ID NO 1
<211> LENGTH: 10
<212> TYPE: PRT
<213> ORGANISM: Mus musculus

<400> SEQUENCE: 1

Gly Tyr Thr Phe Thr Ser Tyr Gly Ile Ser
1               5                   10

<210> SEQ ID NO 2
<211> LENGTH: 17
<212> TYPE: PRT
<213> ORGANISM: Mus musculus

<400> SEQUENCE: 2

Glu Ile Tyr Pro Arg Ser Gly Asn Thr Tyr Tyr Asn Glu Lys Phe Lys
1               5                   10                  15

Gly

<210> SEQ ID NO 3
<211> LENGTH: 11
<212> TYPE: PRT
<213> ORGANISM: Mus musculus

<400> SEQUENCE: 3

Lys Gly Pro Tyr Tyr Thr Lys Asn Glu Asp Tyr
1               5                   10
```

```
<210> SEQ ID NO 4
<211> LENGTH: 11
<212> TYPE: PRT
<213> ORGANISM: Mus musculus

<400> SEQUENCE: 4

Arg Ala Ser Glu His Ile Tyr Tyr Ser Leu Ala
1               5                   10

<210> SEQ ID NO 5
<211> LENGTH: 7
<212> TYPE: PRT
<213> ORGANISM: Mus musculus

<400> SEQUENCE: 5

Asn Ala Asn Ser Leu Glu Asp
1               5

<210> SEQ ID NO 6
<211> LENGTH: 9
<212> TYPE: PRT
<213> ORGANISM: Mus musculus

<400> SEQUENCE: 6

Lys Gln Ala Tyr Asp Val Pro Arg Thr
1               5

<210> SEQ ID NO 7
<211> LENGTH: 120
<212> TYPE: PRT
<213> ORGANISM: Mus musculus

<400> SEQUENCE: 7

Gln Val Gln Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Phe Cys
                85                  90                  95

Ala Arg Lys Gly Pro Tyr Tyr Thr Lys Asn Glu Asp Tyr Trp Gly Gln
            100                 105                 110

Gly Thr Ile Leu Thr Val Ser Ser
        115                 120

<210> SEQ ID NO 8
<211> LENGTH: 116
<212> TYPE: PRT
<213> ORGANISM: Mus musculus

<400> SEQUENCE: 8

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu His Ile Tyr Tyr Ser
            20                  25                  30

Leu Ala Trp Tyr Gln Gln Lys Gln Gly Lys Ser Pro Gln Leu Leu Ile
```

```
                35                  40                  45
Tyr Asn Ala Asn Ser Leu Glu Asp Gly Val Pro Ser Arg Phe Ser Gly
             50                  55                  60

Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Val Pro Arg
                 85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 9
<211> LENGTH: 360
<212> TYPE: DNA
<213> ORGANISM: Mus Musculus

<400> SEQUENCE: 9
caggtgcagc tgcaggagtc tggagctgag ctggcgaggc ctggggcttc agtgaagctg      60
tcctgcaagg cttctggcta caccttcaca agctatggta taagctgggt gaagcagaga     120
actggacagg gccttgagtg gattggagag atttatccca agagtggtaa tacttactac     180
aatgagaagt tcaagggcaa ggccacactg actgcagaca atcctccag cacagcgtac      240 atggagctca gcagcctgac atctgaggac tctgcggtct atttctgtgc aagaaaggga     300
ccctactata ctaagaacga ggactactgg ggccaaggca ccattctcac agtctcctca     360

<210> SEQ ID NO 10
<211> LENGTH: 348
<212> TYPE: DNA
<213> ORGANISM: Mus musculus

<400> SEQUENCE: 10
gacatccaga tgactcagtc tccagcctcc ctggctgcat ctgtgggaga aactgtcacc      60
atcacatgtc gagcaagtga gcacatttac tacagtttag catggtatca gcagaagcaa     120
gggaaatctc ctcagctcct gatctataat gcaaacagct ggaagatgg tgtcccatcg      180 aggttcagtg gcagtggatc tgggacacaa tattctatga agatcaacag catgcagcct     240
gaagataccg caacttattt ctgtaaacag gcttatgacg ttcctcggac cttcggtgga     300
ggcaccaagc tggaaatcaa acgggctgat gctgcaccaa ctgtatcc                  348

<210> SEQ ID NO 11
<211> LENGTH: 6
<212> TYPE: PRT
<213> ORGANISM: Mus musculus

<400> SEQUENCE: 11

Thr Ser Tyr Gly Ile Ser
1               5

<210> SEQ ID NO 12
<211> LENGTH: 5
<212> TYPE: PRT
<213> ORGANISM: Mus musculus

<400> SEQUENCE: 12

Ile Tyr Cys Ile His
1               5
```

```
<210> SEQ ID NO 13
<211> LENGTH: 17
<212> TYPE: PRT
<213> ORGANISM: Mus musculus

<400> SEQUENCE: 13

Glu Ile Ser Pro Ser Asn Gly Arg Thr Ile Tyr Asn Glu Lys Phe Lys
1               5                   10                  15

Asn

<210> SEQ ID NO 14
<211> LENGTH: 11
<212> TYPE: PRT
<213> ORGANISM: Mus musculus

<400> SEQUENCE: 14

Ser Asp Gly Tyr Asp Gly Tyr Tyr Phe Asp Tyr
1               5                   10

<210> SEQ ID NO 15
<211> LENGTH: 11
<212> TYPE: PRT
<213> ORGANISM: Mus musculus

<400> SEQUENCE: 15

Arg Ala Ser Gln Glu Ile Ser Gly Tyr Leu Asn
1               5                   10

<210> SEQ ID NO 16
<211> LENGTH: 7
<212> TYPE: PRT
<213> ORGANISM: Mus musculus

<400> SEQUENCE: 16

Ala Ala Ser Thr Leu Asp Ser
1               5

<210> SEQ ID NO 17
<211> LENGTH: 9
<212> TYPE: PRT
<213> ORGANISM: Mus musculus

<400> SEQUENCE: 17

Leu Gln Tyr Ala Ser Tyr Pro Arg Thr
1               5

<210> SEQ ID NO 18
<211> LENGTH: 120
<212> TYPE: PRT
<213> ORGANISM: Mus musculus

<400> SEQUENCE: 18

Gln Val Gln Leu Leu Gln Pro Gly Ala Glu Leu Val Lys Pro Gly Ala
1               5                   10                  15

Ser Val Lys Leu Ser Cys Lys Ala Ser Gly Tyr Thr Phe Thr Ile Tyr
                20                  25                  30

Cys Ile His Trp Val Lys Gln Arg Pro Gly Gln Gly Leu Glu Trp Ile
            35                  40                  45

Gly Glu Ile Ser Pro Ser Asn Gly Arg Thr Ile Tyr Asn Glu Lys Phe
        50                  55                  60

Lys Asn Lys Ala Thr Leu Thr Ile Asp Lys Ser Ser Thr Thr Ala Tyr
65                  70                  75                  80
```

Met Gln Leu Ser Ser Leu Thr Ser Glu Asp Ser Ala Val Tyr Cys Cys
            85                  90                  95

Ala Ile Ser Asp Gly Tyr Asp Gly Tyr Tyr Phe Asp Tyr Trp Gly Gln
            100                 105                 110

Gly Thr Thr Leu Thr Val Ser Ser
        115                 120

<210> SEQ ID NO 19
<211> LENGTH: 107
<212> TYPE: PRT
<213> ORGANISM: Mus musculus

<400> SEQUENCE: 19

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Asn Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Arg Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 20
<211> LENGTH: 360
<212> TYPE: DNA
<213> ORGANISM: Mus musculus

<400> SEQUENCE: 20
caggtccaac tgctgcagcc tggggctgaa ctggtgaagc ctggggcttc agtgaagctg      60
tcctgcaagg cttctggcta caccttcacc atctactgta cactgggt gaagcagagg       120 cctggacaag gccttgagtg gattggagag attagtccta gcaacggtcg tactatctac     180
aatgagaagt tcaagaacaa ggccacactg actatagaca atcctccac acagcctac      240 atgcaactca gcagcctgac atctgaggac tctgcggtct attgctgtgc aatatcggat     300
ggttacgacg gatactactt tgactactgg ggccaaggca ccactctcac agtctcctca     360

<210> SEQ ID NO 21
<211> LENGTH: 321
<212> TYPE: DNA
<213> ORGANISM: Mus musculus

<400> SEQUENCE: 21
gacatccaga tgacccagtc tccatcctcc ttatctgcct ctctgggaga aagagtcagt      60
ctcacttgtc gggcaagtca ggaaattagt ggttacttaa actggcttca gcagaaacca     120
gatggaacta ttaaacgcct gatctacgcc gcatccactt tagattctgg tgtcccaaaa     180
aggttcagtg gcagtaggtc tgggtcagat tattctctca ccatcagcag acttgagtct     240
gaagattttg cagactatta ctgtctacaa tatgctagtt atcctcggac gttcggtgga     300
ggcaccaagc tggaaatcaa a                                                321